US009895052B2

(12) United States Patent
Okamoto

(10) Patent No.: US 9,895,052 B2
(45) Date of Patent: Feb. 20, 2018

(54) INSERTION INSTRUMENT AND INSERTION APPARATUS COMPRISING THIS INSERTION INSTRUMENT

(71) Applicant: OLYMPUS CORPORATION, Tokyo (JP)

(72) Inventor: Yasuhiro Okamoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/060,768

(22) Filed: Mar. 4, 2016

(65) Prior Publication Data
US 2016/0183769 A1 Jun. 30, 2016

Related U.S. Application Data

(63) Continuation of application No. PCT/JP2014/080510, filed on Nov. 18, 2014.

(30) Foreign Application Priority Data

Nov. 20, 2013 (JP) .................................. 2013-240320
Nov. 20, 2013 (JP) .................................. 2013-240321
Mar. 11, 2014 (JP) .................................. 2014-048078

(51) Int. Cl.
*A61B 1/00* (2006.01)
*A61B 1/04* (2006.01)
(Continued)

(52) U.S. Cl.
CPC ........ *A61B 1/0052* (2013.01); *A61B 1/00006* (2013.01); *A61B 1/00009* (2013.01);
(Continued)

(58) Field of Classification Search
CPC ............ A61B 1/00064; A61B 1/00066; A61B 1/00068; A61B 1/00071; A61B 1/005;
(Continued)

(56) References Cited

U.S. PATENT DOCUMENTS

2006/0030751 A1* 2/2006 Uesugi ............... A61B 1/00068
600/101
2006/0276689 A1* 12/2006 Litscher ............. A61B 1/00103
600/156
(Continued)

FOREIGN PATENT DOCUMENTS

JP 2006-320501 A 11/2006
WO WO 2012/063880 A1 5/2012
(Continued)

OTHER PUBLICATIONS

English translation of International Preliminary Report on Patentability dated Jun. 2, 2016, together with the Written Opinion received in related International Application No. PCT/JP2014/080510.
(Continued)

*Primary Examiner* — Anhtuan T Nguyen
*Assistant Examiner* — William Chou
(74) *Attorney, Agent, or Firm* — Scully, Scott, Murphy & Presser, P.C.

(57) ABSTRACT

An insertion instrument includes an insertion portion having a curving portion, and an operation portion body coupled to the proximal side of the insertion portion. The operation portion body includes a first surface, and a second surface extending from the first surface and extending in a direction different from the direction in which the first surface extends. A finger side other than a thumb of a grasping hand is located in the second surface. The operation portion body includes a first curving operation portion which is provided in the first surface and which curves the curving portion in a first direction, a functional switch which is provided in the second surface and which operates a predetermined function of the insertion instrument, and a second curving operation portion which is provided in the second surface.

10 Claims, 22 Drawing Sheets

(51) Int. Cl.
*A61B 1/06* (2006.01)
*A61B 1/005* (2006.01)
*G02B 23/24* (2006.01)
*A61B 1/045* (2006.01)

(52) U.S. Cl.
CPC .......... *A61B 1/0016* (2013.01); *A61B 1/0055* (2013.01); *A61B 1/00068* (2013.01); *A61B 1/045* (2013.01); *G02B 23/24* (2013.01)

(58) Field of Classification Search
CPC ... A61B 1/0051; A61B 1/0052; A61B 1/0053; A61B 1/0055; A61B 1/0056; A61B 1/0057; A61B 1/0058; A61B 1/008; A61B 1/015; A61B 1/12
USPC ........ 600/102, 104, 109, 114, 117, 118, 131, 600/139–160; 348/45, 65
See application file for complete search history.

(56) References Cited

U.S. PATENT DOCUMENTS

2010/0022837 A1\* 1/2010 Ishiguro ................ A61B 17/29
600/127
2012/0302829 A1\* 11/2012 Omoto ................ A61B 1/0052
600/109

FOREIGN PATENT DOCUMENTS

WO    WO 2012/074013 A1    6/2012
WO    WO 2013/129494 A1    9/2013

OTHER PUBLICATIONS

International Search Report dated Mar. 3, 2015 issued in PCT/JP2014/080510.

\* cited by examiner

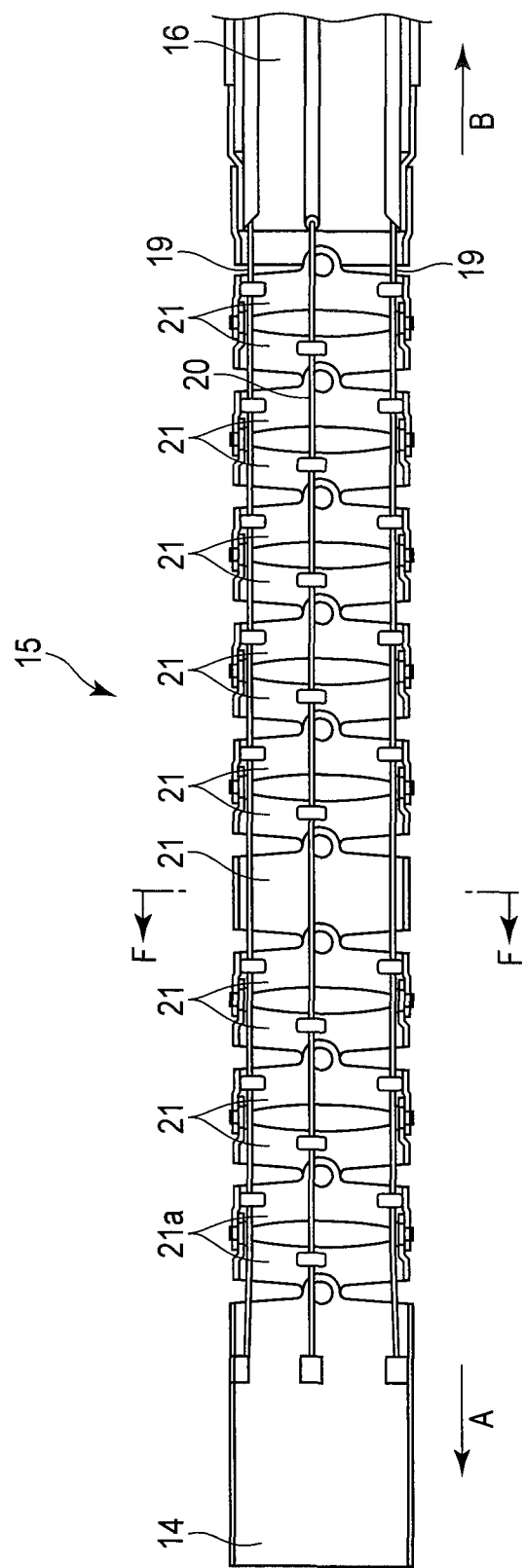
F I G. 2

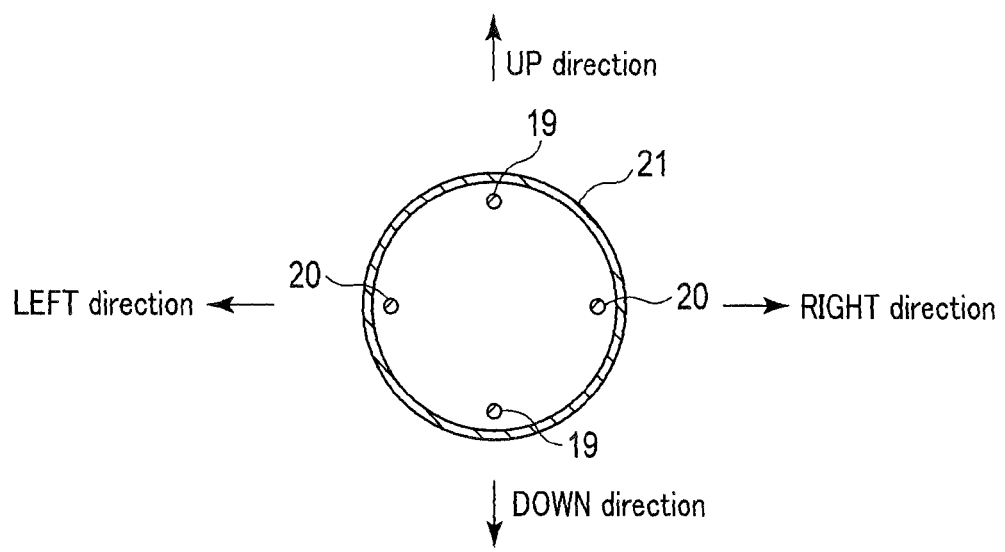
F I G. 3
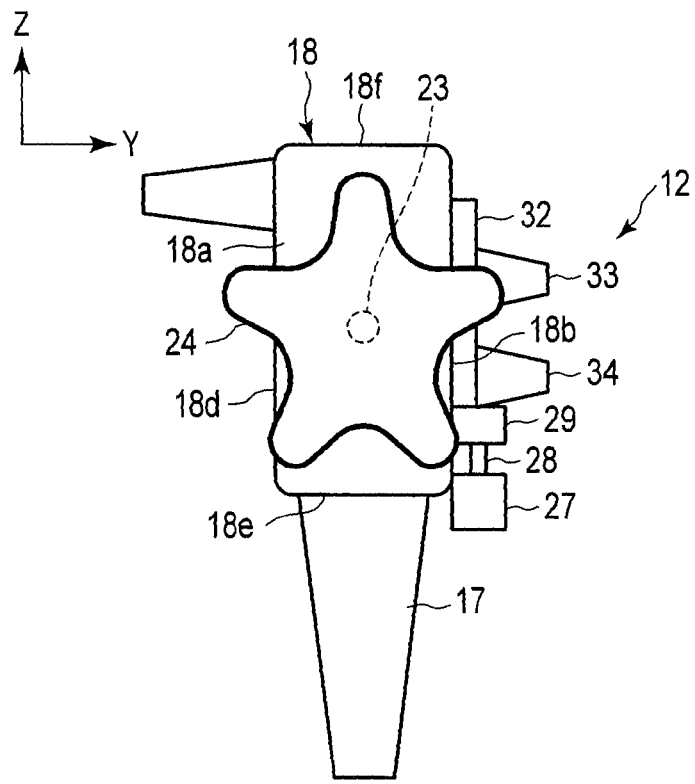
F I G. 4

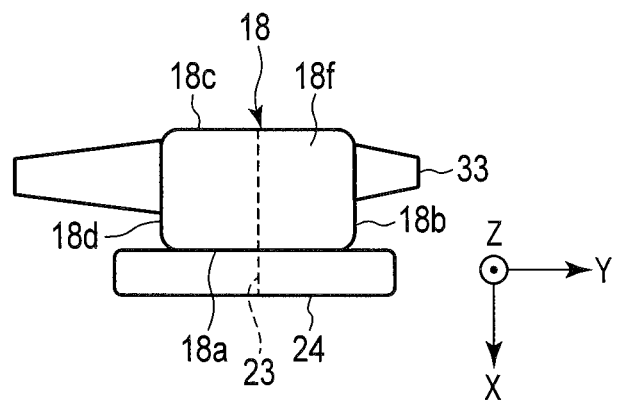
F I G. 5
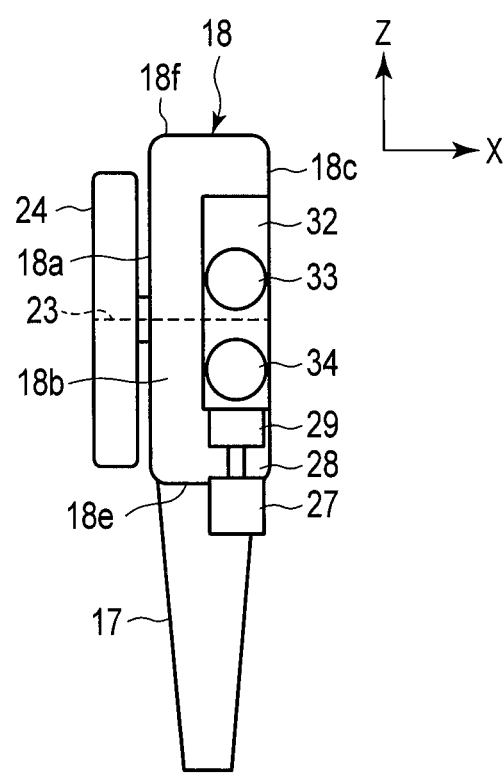
F I G. 6

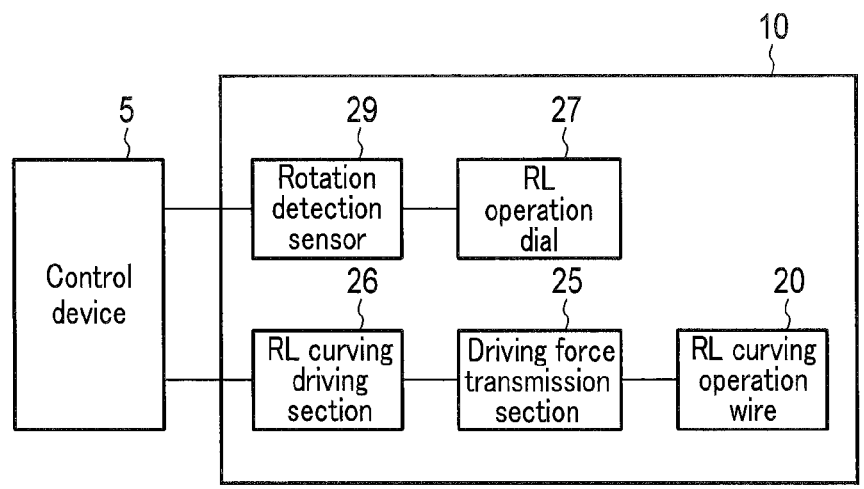
F I G. 9
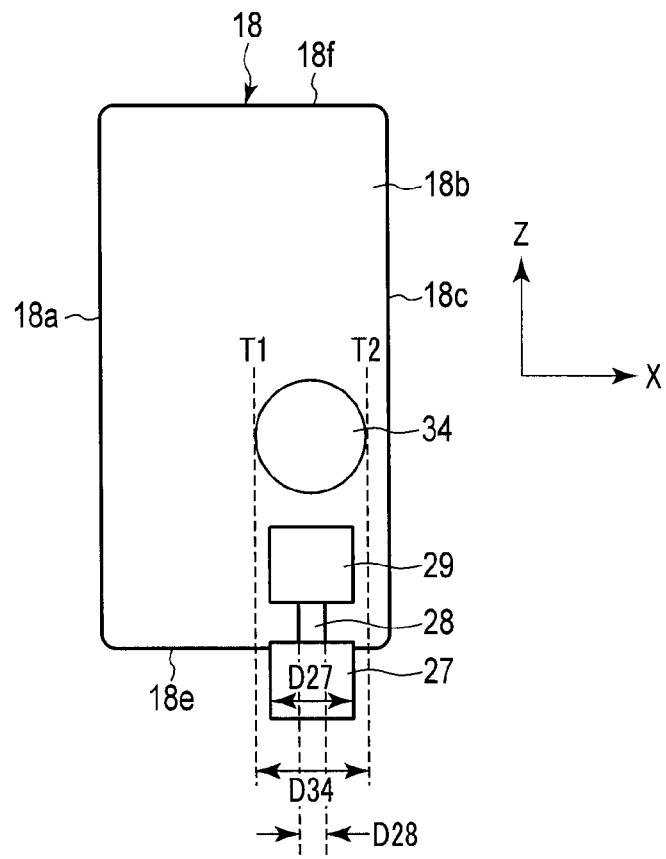
F I G. 10

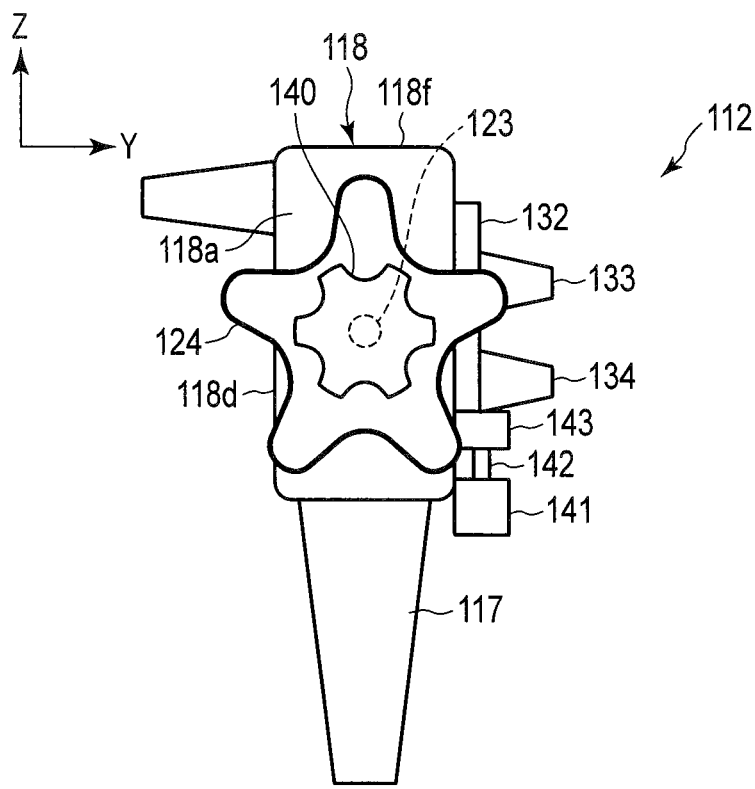
F I G. 13
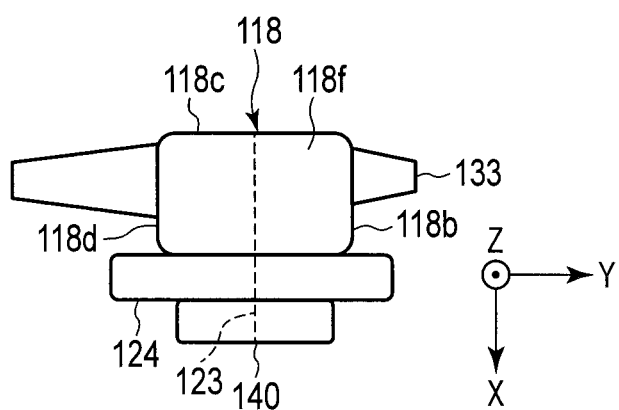
F I G. 14

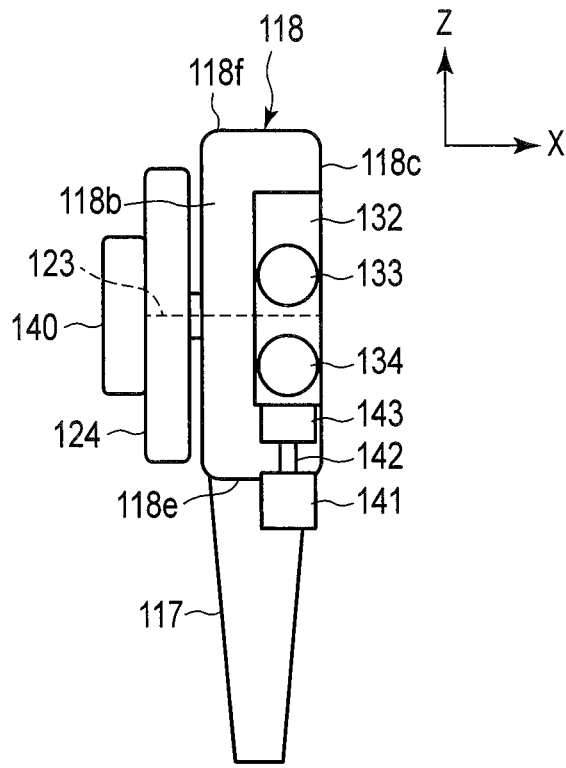
F I G. 15
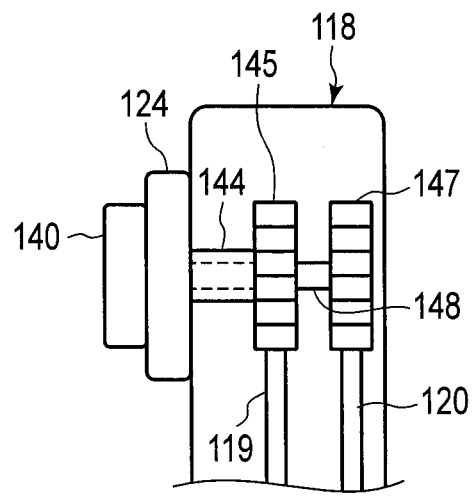
F I G. 16

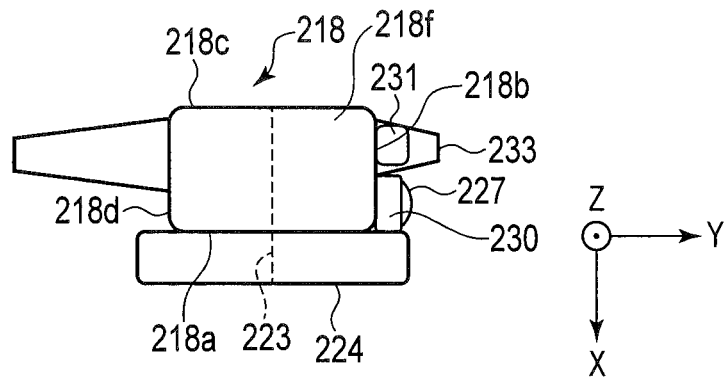
F I G. 19
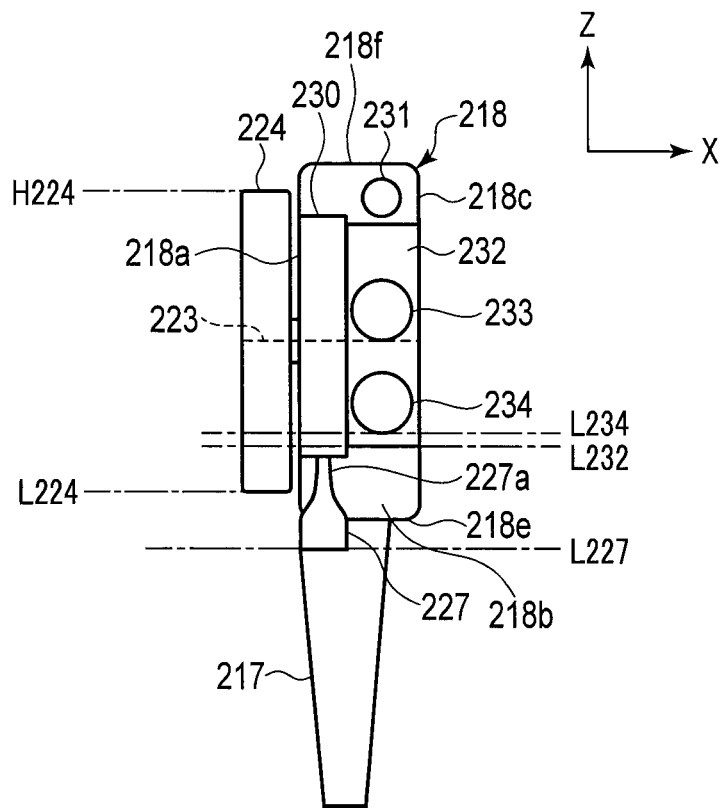
F I G. 20

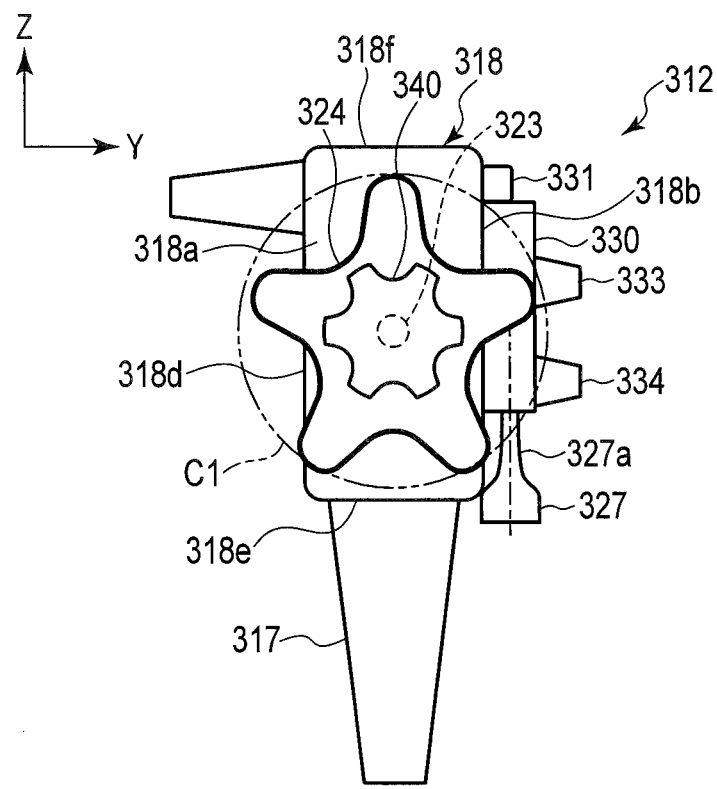
F I G. 22
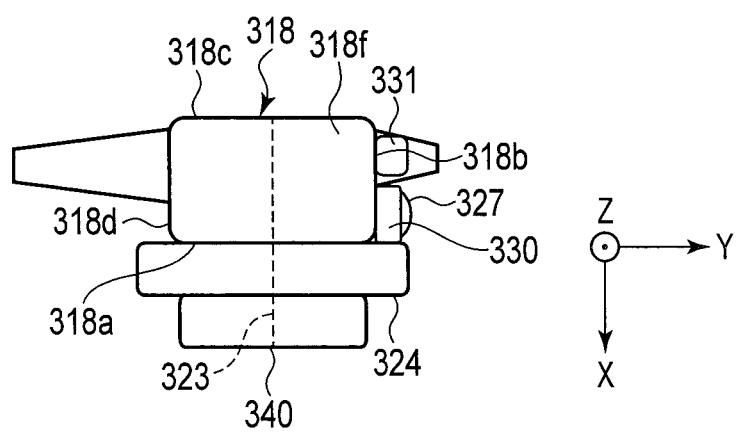
F I G. 23

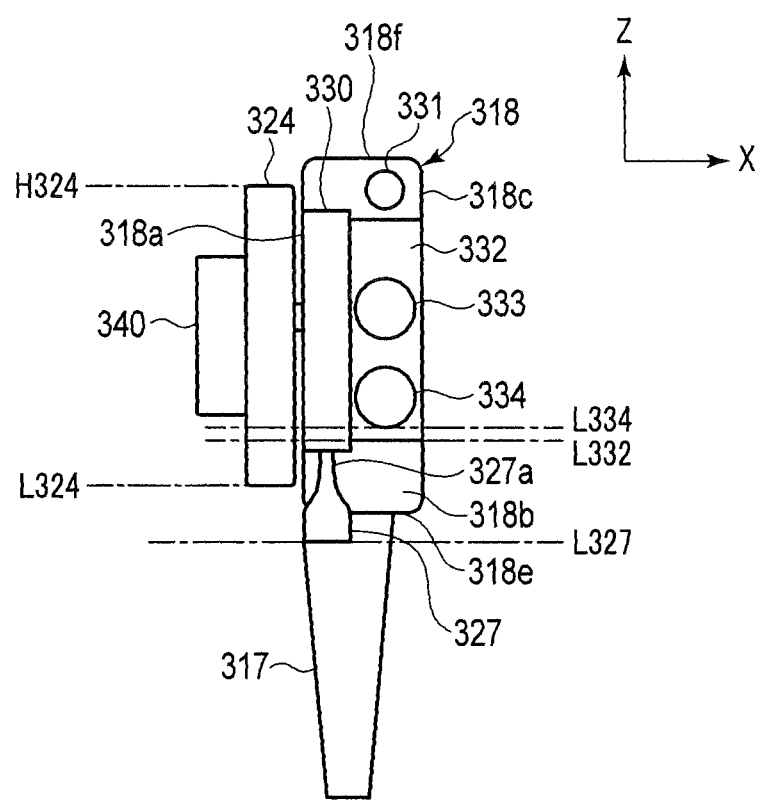
F I G. 24

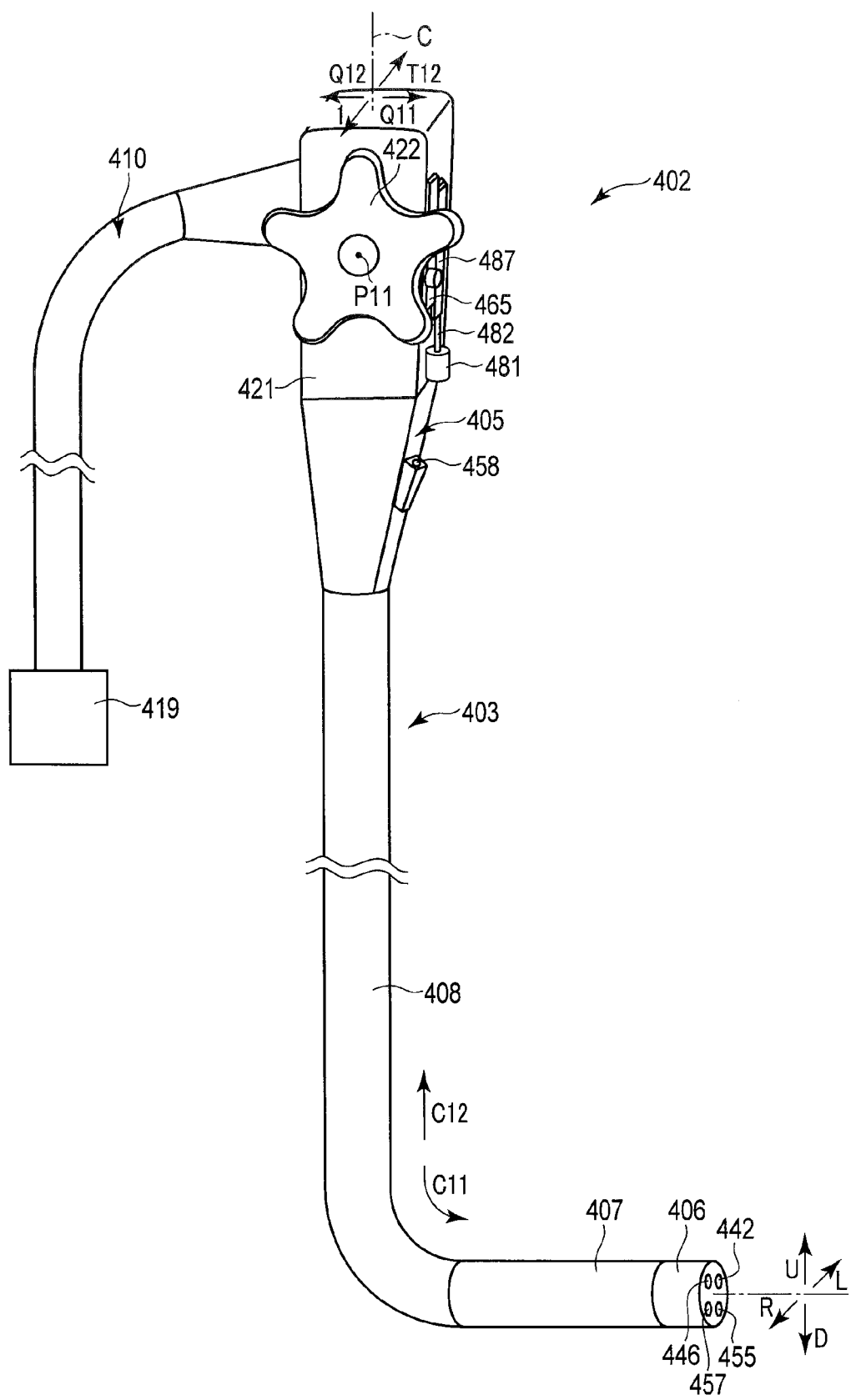
F I G. 26

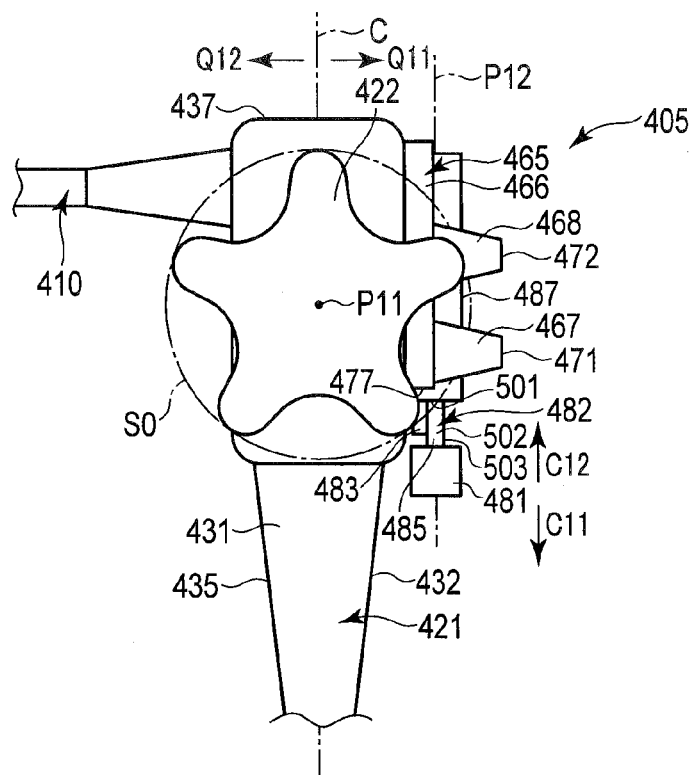
F I G. 27
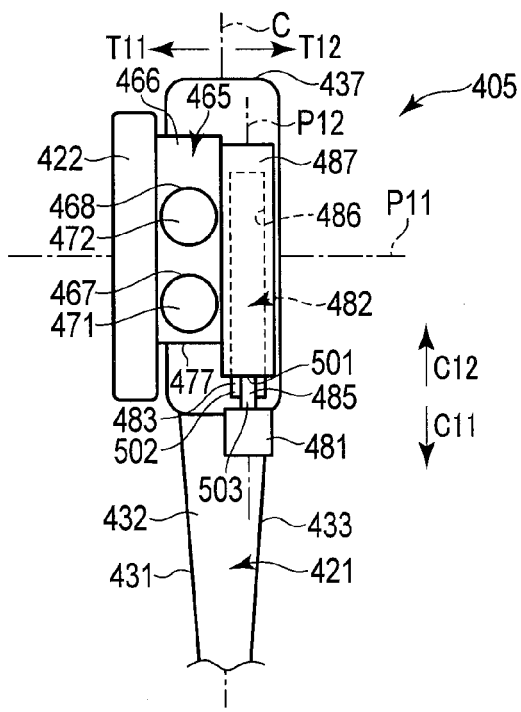
F I G. 28

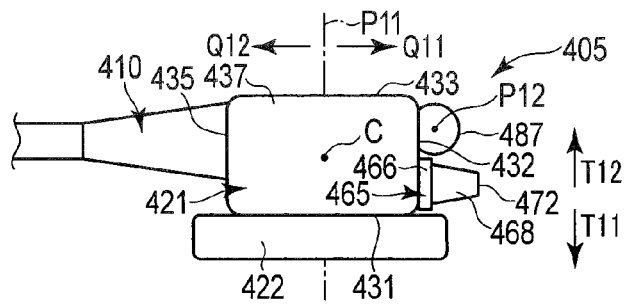
F I G. 29
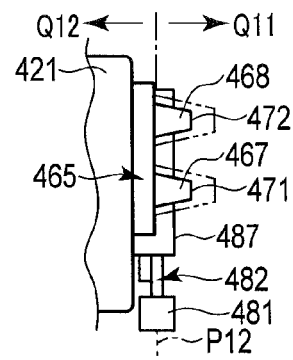
F I G. 30
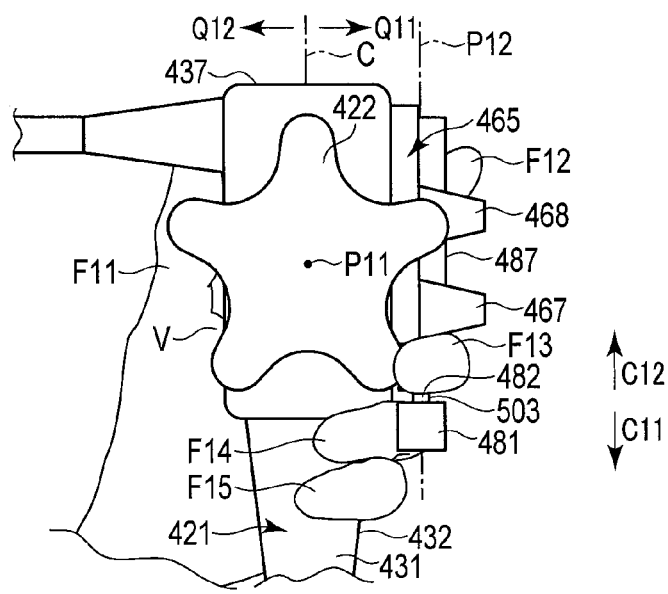
F I G. 31

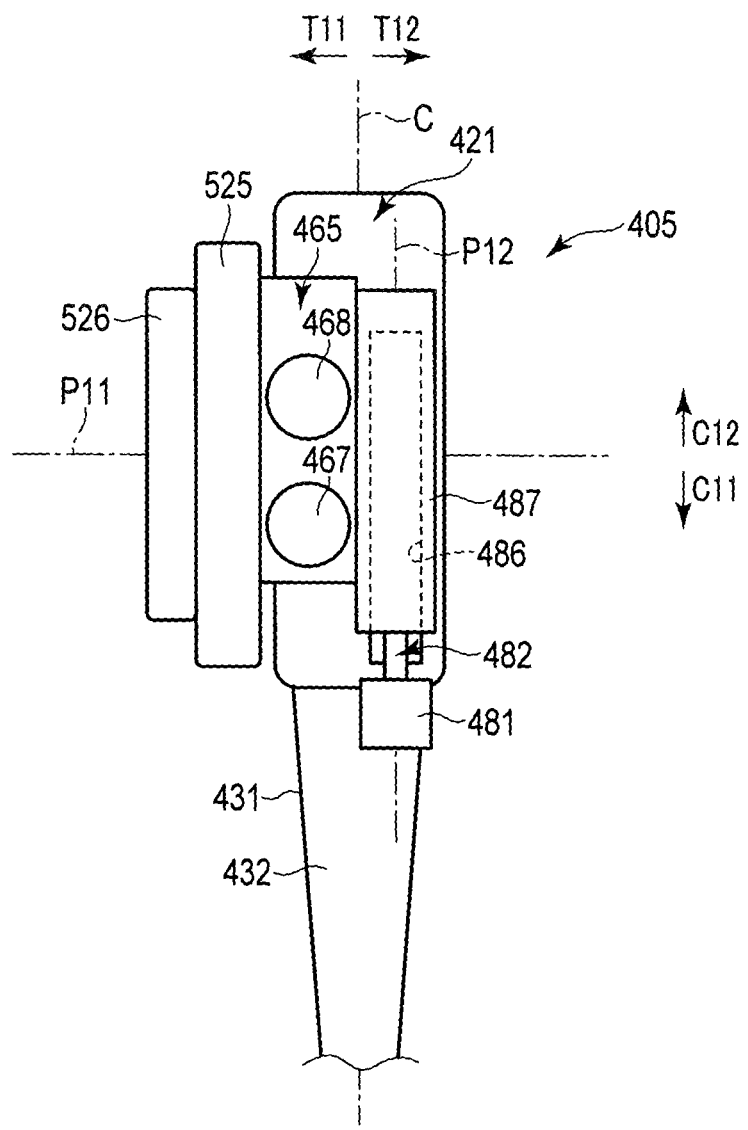
F I G. 35

INSERTION INSTRUMENT AND INSERTION APPARATUS COMPRISING THIS INSERTION INSTRUMENT

CROSS-REFERENCE TO RELATED APPLICATIONS

This is a Continuation Application of PCT Application No. PCT/JP2014/080510, filed Nov. 18, 2014, which was published under PCT Article 21(2) in Japanese.

This application is based upon and claims the benefit of priority from prior the Japanese Patent Application No. 2013-240320, filed Nov. 20, 2013; No. 2013-240321, filed Nov. 20, 2013; and No. 2014-048078, filed Mar. 11, 2014 the entire contents each of which are incorporated herein by references.

BACKGROUND OF THE INVENTION

1. Field of the Invention

The present invention relates to an insertion instrument comprising a curving portion on the distal side of an insertion portion. The present invention also relates to an insertion instrument in which an action portion is provided in an insertion portion extending along a longitudinal axis, and an insertion apparatus comprising this insertion instrument.

2. Description of the Related Art

In general, an insertion apparatus having an elongated insertion portion to be inserted into a specimen, for example, an endoscope is widely used. Such an endoscope has an insertion portion comprising a curving portion at the distal side, and a curving operation portion to curve the curving portion. When such an endoscope is used to, for example, observe and treat, for example, a lesion in the specimen, the curving operation portion is operated to curve the curving portion in a desired direction and insert the curving portion into the specimen at the same time.

For example, Patent Literature 1: International Publication No. 2012/074013 discloses an endoscope provided with, as curving operation portions, a UD curving operation knob for curving a curving portion in an up/down (UD) direction, and an RL curving operation dial for curving the curving portion in a right/left (RL) direction. The UD curving operation knob is provided in an operation portion body of the endoscope along its longitudinal axis, and the RL curving operation dial is provided in the operation portion body in the vicinity of the lower side of the UD curving operation knob. The curving portion is mechanically curved in the UD direction if an operator rotates the UD curving operation knob. The curving portion is curved in the RL direction by driving force from a motor which is driven if the operator rotates the RL curving operation dial. That is, the curving in the RL direction is electrically driven.

For example, Patent Literature 2: Jpn. Pat. Appln. KOKAI Publication No. 2006-320501 discloses an endoscope comprising a curving portion composed of a distal-side first curving portion and a proximal-side second curving portion to insert an insertion portion into a specimen along the bending shape of the specimen. The first curving portion and the second curving portion are respectively curved in the UD direction and the RL direction independently of each other by the rotation operations of a UD curving operation knob and an RL curving operation knob for curving the first curving portion and by the rotation operation of a UD curving operation knob for curving the second curving portion.

In the endoscope disclosed in Patent Literature 1: International Publication No. 2012/074013, a curving portion which is an action portion is provided at the distal end of an insertion portion, and a holding portion is provided closer to the proximal direction side than the insertion portion. The curving portion performs a first action to curve in first perpendicular directions which are two directions perpendicular to a longitudinal axis, and a second action to curve in second perpendicular directions which are two directions perpendicular to the longitudinal axis and perpendicular to a first curving direction. The holding portion comprises a holding portion casing, and a curving operation knob which a first operation input portion rotatable relative to the holding portion casing around a rotation axis perpendicular to the longitudinal axis. The first operation to operate the first action of the curving portion is input by the rotation of the curving operation knob.

Here, one of directions parallel to the rotation axis is a first rotation axis direction, and a direction opposite to the first rotation axis direction is a second rotation axis direction. One of directions perpendicular to the longitudinal axis and perpendicular to the rotation axis is a first perpendicular direction, and a direction opposite to the first perpendicular direction is a second perpendicular direction. A holding portion housing comprises a first casing outer surface which faces in the first rotation axis direction and in which the curving operation knob is disposed, and a second casing outer surface which faces in the first perpendicular direction. A curving operation dial which is a second operation input portion is provided in the second casing outer surface. A second operation to operate the second action of the curving portion is input by the rotation of the curving operation dial around a drive axis. The drive axis extends from the curving operation dial toward the proximal direction side in such a manner as to cross over the rotation axis. The curving operation dial is located closer to the distal direction side than the curving operation knob.

A button unit which comprises operation buttons such as air/liquid supply operation button is provided on the second casing outer surface. In a longitudinal axis direction parallel to the longitudinal axis, the position of the button unit substantially corresponds to the position of the curving operation knob. Paths such as an air supply path and a liquid supply path extend through the holding portion, and air/liquid valves are disposed as functional units in the air supply path and the liquid supply path. A switch operation to switch on and off (the operation states of) the air/liquid valves in the air supply path and the liquid supply path is input by the air/liquid supply operation button.

BRIEF SUMMARY OF THE INVENTION

According to an embodiment of the present invention, there is provided an insertion instrument comprising: an insertion portion having a curving portion; and an operation portion body coupled to the proximal side of the insertion portion, the operation portion body comprising a first surface, and a second surface extending from the first surface and extending in a direction different from the direction in which the first surface extends, a finger side other than a thumb of a grasping hand being located in the second surface, wherein the operation portion body comprises a first curving operation portion which is provided in the first surface and which curves the curving portion in a first direction, a functional switch which is provided in the second surface and which turns on a predetermined function of the insertion instrument, and a second curving operation portion which is provided in the second surface and which comprises a first rotation axis and which is rotated around the first rotation axis to curve the curving portion in a second direction, and the rotation axis is located between two tangents of the functional switch parallel to a longitudinal axis of the operation portion body.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 2 is a sectional view of an insertion portion in a longitudinal axis direction mainly showing the internal structure of a curving portion;

FIG. 3 is a sectional view taken along the line F-F shown in FIG. 2;

FIG. 4 is a front view of an endoscope body in an YZ plane;

FIG. 5 is a top view of the endoscope body in an XY plane;

FIG. 6 is a side view of the endoscope body in the XZ plane;

FIG. 9 is a block diagram schematically showing control regarding an RL curving operation of the curving portion;

FIG. 10 is a diagram schematically showing one aspect of the positional relation between a switch and an RL operation dial in an operation portion body of the endoscope body;

FIG. 13 is a front view of an endoscope body in the YZ plane;

FIG. 14 is a top view of the endoscope body in the XY plane;

FIG. 15 is a side view of the endoscope body in the XZ plane;

FIG. 16 is a diagram schematically showing the mechanism of the endoscope body regarding the UD curving operation and the RL curving operation of a first curving portion and a second curving portion;

FIG. 19 is a top view of an endoscope body in the XY plane;

FIG. 20 is a side view of the endoscope body in the XZ plane;

FIG. 22 is a front view of an endoscope body in the YZ plane according to a fourth embodiment of the present invention;

FIG. 23 is a top view of the endoscope body in the XY plane;

FIG. 24 is a side view of the endoscope body in the XZ plane;

FIG. 26 is a perspective view schematically showing an endoscope according to the fifth embodiment;

FIG. 27 is a schematic diagram in which a holding portion of the endoscope is seen from a first rotation axis direction side;

FIG. 28 is a schematic diagram in which a holding portion of the endoscope is seen from a first perpendicular direction side;

FIG. 29 is a schematic diagram in which the holding portion of the endoscope is seen from a proximal direction side;

FIG. 30 is a schematic diagram showing the configurations of a button unit and a housing portion formation surface;

FIG. 31 is a schematic diagram seen from the first rotation axis direction side showing how a holding portion casing is held with the left hand;

FIG. 35 is a schematic diagram in which a holding portion of the endoscope according to the second modification is seen from the first perpendicular direction side.

DETAILED DESCRIPTION OF THE PREFERRED EMBODIMENT

Hereinafter, embodiments of the present invention will be described. An endoscope and an endoscope apparatus are described below as examples of an insertion instrument and an insertion apparatus.

First Embodiment

The first embodiment of the present invention is described with reference to FIG. 1 to FIG. 11.

Figure 1:
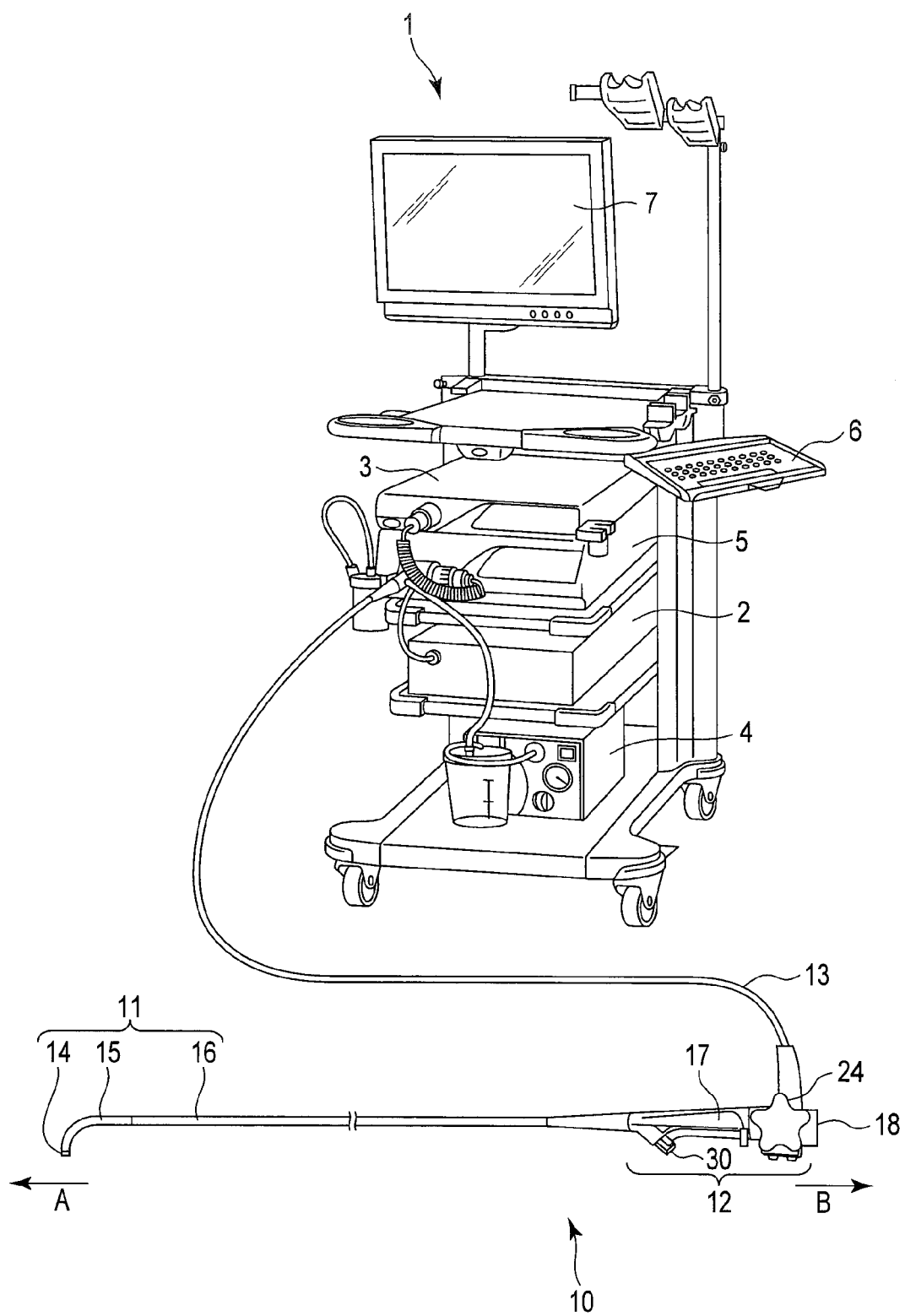
FIG. 1 is a general view schematically showing an endoscope apparatus including an endoscope according to a first embodiment of the present invention.

FIG. 1 is a general view schematically showing an endoscope apparatus 1 including an endoscope 10 according to the first embodiment. The endoscope apparatus 1 has the endoscope 10, a light source device 2, a video processor device 3, an air/water supply device 4, a control device 5 which controls the endoscope 10 and the devices 2 to 4, an input keyboard 6 for these devices, and a monitor 7.

The light source device 2 supplies illumination light to an illumination optical system (indicated with an arrow A in FIG. 1) on the endoscope distal side. The video processor device 3 processes a signal of an image obtained from an observation optical system on the endoscope distal side and outputs a video signal, and the output image is displayed on the monitor 7. The air/water supply device 4 properly supplies air/liquid to the endoscope 10.

The endoscope 10 has an elongated insertion portion 11 on the endoscope distal side, an endoscope body 12 on an endoscope proximal side (indicated with an arrow B in FIG. 1) coupled to the proximal side of the insertion portion 11, and a universal cord 13 which extends from the endoscope body 12 and which includes a light guide and an electric cable. The endoscope 10 is removably connected to the light source device 2, the video processor device 3, the air/water supply device 4, and the control device 5 via the universal cord 13, and communicates with these devices.

The insertion portion 11 is an elongated tube on the endoscope distal side, and is inserted into a specimen. The insertion portion 11 has a rigid distal portion 14 at the distalmost end of the insertion portion, a curving portion 15 provided on the proximal side of the distal portion, and a long and flexible tube 16 provided on the proximal side of the curving portion.

The outer circumferential surface of the distal portion 14 can be made of a rigid material such as stainless steel, and is covered with a synthetic resin cover. Although not shown, the distal portion 14 has therein an observation optical system including an objective lens disposed in the distal surface, a CCD which focuses an optical image obtained from the observation optical system and then converts the optical image into an electric signal, an illumination optical system including an illumination lens disposed in the distal surface, a light guide which transmits the illumination light to the illumination optical system, and air/liquid supply channels for lens cleaning or for the suction of liquids and tissues in the specimen. The light guide and the air/liquid supply channels extend to the distal side of the universal cord 13 from the insertion portion 11 through the endoscope body 12.

FIG. 2 is a sectional view of the insertion portion 11 in a longitudinal axis direction mainly showing the internal structure of the curving portion 15. FIG. 3 is a sectional view taken along the line F-F shown in FIG. 2. A UD curving operation wire 19 for curving the curving portion 15 in an up/down (hereinafter referred to as UD) direction as a first direction, and an RL curving operation wire 20 for curving the curving portion 15 in a right/left (hereinafter referred to as RL) direction as a second direction are inserted through the curving portion 15 and the flexible tube 16. The UD direction and the RL direction are directions that intersect at right angles with each other as shown in FIG. 3.

As shown in FIG. 2, the curving portion 15 has curving pieces 21 arranged in the longitudinal axis direction of the insertion portion 11. These curving pieces 21 are joined rotatably relative to one another. The curving pieces 21 is covered with a braid in which thin wires are braided into a cylindrical shape, and the outer circumference of the braid is covered with a cylindrical curving rubber including, for example, fluoro-rubber.

The flexible tube 16 is a flexible, long, and soft portion, and its outermost layer is made of a heat-resistant and chemical-resistant material such as a fluorocarbon resin material.

Figure 8:
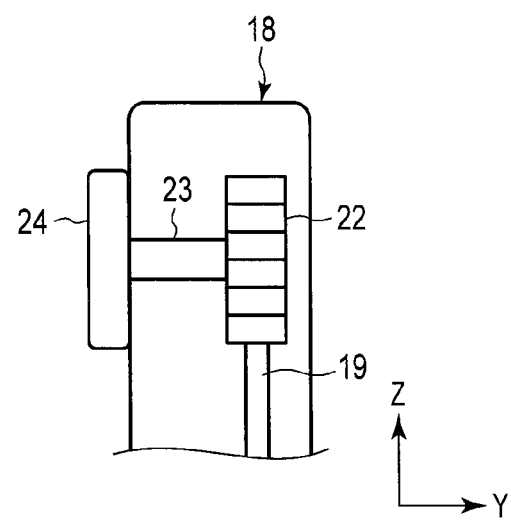
FIG. 8 is a diagram schematically showing the mechanism of the endoscope body regarding a UD curving operation of the curving portion.

In the curving portion 15, the distal end of the UD curving operation wire 19 is coupled to the distalmost curving piece 21a at a position corresponding to the U-direction and D-direction of the curving portion 15. The UD curving operation wire 19 extends into the endoscope body 12 from the distalmost curving piece 21a of the curving portion 15 through the flexible tube 16, and its proximal end is wound around a later-described turning drum 22 in the endoscope body 12 (FIG. 8).

The distal end of the RL curving operation wire 20 is also coupled to the distalmost curving piece 21a at a position corresponding to the R-direction and L-direction of the curving portion 15. The RL curving operation wire 20 extends into the endoscope body 12 from the distalmost curving piece 21a of the curving portion 15 through the flexible tube 16, and its proximal end is coupled to a later-described driving force transmission portion 25 in the endoscope body 12 (FIG. 9).

Figure 7:
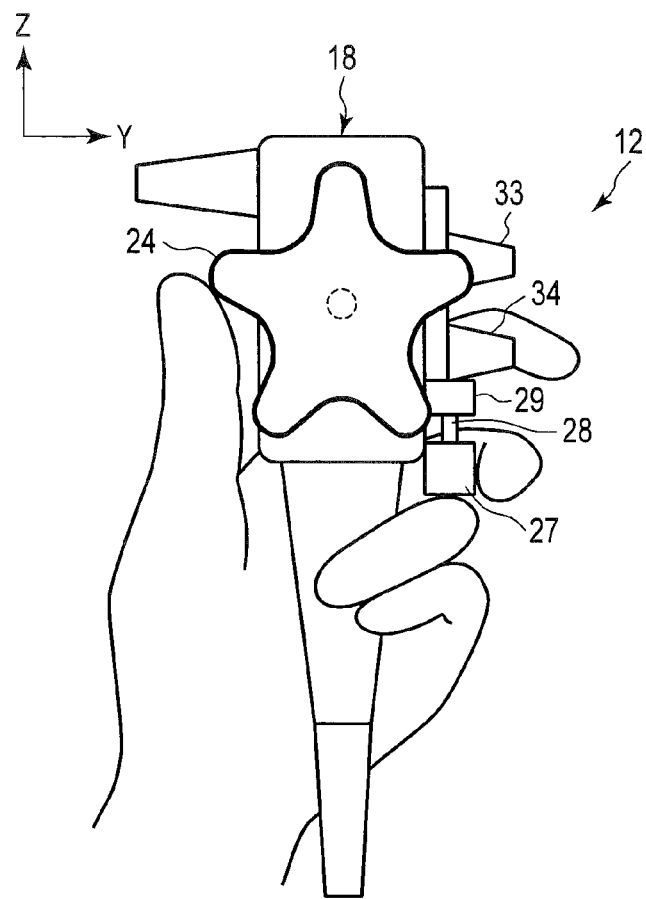
FIG. 7 is a front view in the YZ plane in which an operator is grasping the endoscope body.

FIG. 4 to FIG. 6 are a front view, a top view, and a side view of the endoscope body 12, respectively. FIG. 7 is a front view in which an operator is grasping the endoscope body 12. In FIG. 4 to FIG. 7, the longitudinal axis direction of the endoscope body 12 is a Z-direction, a direction which intersects at right angles with the longitudinal axis direction and in which the universal cord 13 extends from the endoscope body 12 is a Y-direction, and the thickness direction of the endoscope body 12 that intersects at right angles with the Y-direction and the Z-direction is an X-direction.

The endoscope body 12 has a grip portion 17 coupled to the proximal end of the flexible tube 16, and an operation portion body 18 which is located on the proximal side of the grip portion 17 and which is integral with the grip portion 17. The grip portion 17 is tapered to decrease in diameter toward its distal end. When the endoscope body 12 is grasped by the operator (e.g. a doctor), the grip portion 17 is on the lower side, and the operation portion body 18 is on the upper side as shown in FIG. 7.

As shown in FIG. 1, a forceps insertion hole 30 is provided in the grip portion 17. The forceps insertion hole 30 is in communication with an unshown forceps channel formed in the insertion portion 11. A treatment instrument such as an ultrasonic probe or a biopsy forceps is inserted into the forceps insertion hole 30 to resect a lesion in the specimen, stop bleeding, and conduct biopsy. The forceps insertion hole 30 and the forceps channel may be used as a suction hole and a suction channel.

The operation portion body 18 has first to sixth surfaces 18a to 18f that form an outer envelope. By way of example, the first surface 18a is located substantially on the right side of the operator when the operator holds the endoscope body 12 in its front surface. The second surface 18b is located distally from the operator. The third surface 18c is located substantially on the left side of the operator. The fourth surface 18d faces the operator. The fifth surface 18e is located substantially on the upper side of the operator. The sixth surface 18f is located substantially on the lower side of the operator.

The first surface 18a is a surface extending along the same longitudinal axis direction as the insertion portion 11 of the endoscope body 12.

The second surface 18b is provided to extend in the circumferential direction of the longitudinal axis from the first surface 18a and extend toward a direction different from the direction in which the first surface 18a extends. The second surface 18b is a surface in which the fingers (the first finger, the second finger, the third finger, and the little finger) other than the thumb of the grasping hand are located when the operator grasps the endoscope body 12. For example, the second surface 18b extends from the first surface 18a, and extends toward the axial direction of a rotation shaft 23 of a later-described UD curving operation knob 24.

The third surface 18c is provided at a position facing the first surface 18a (opposite to the first surface 18a) across the longitudinal axis of the endoscope body 12, and is a surface in which the palm of the hand grasping the endoscope body 12 is located. The third surface 18c may be parallel to the first surface 18a, or may be inclined relative to the first surface 18a to suit to the palm. The second surface 18b is provided continuously with the third surface 18c.

The fourth surface 18d extends from the first surface 18a, extends toward the axial direction of a rotation shaft 23 of the later-described UD curving operation knob 24, is provided continuously with the third surface 18c, and is a surface in which the thumb side of the hand grasping the endoscope body 12 is located. The fourth surface 18d is provided at a position facing the second surface 18b across the longitudinal axis of the endoscope body 12. The fourth surface 18d may be parallel to the second surface 18b, or may be inclined relative to the second surface 18b to suit to the thumb.

The outer envelope of the endoscope body 12 is substantially cylindrically shaped by the first to fourth surfaces 18a, 18b, 18c, and 18d. The size of the endoscope body 12 around the longitudinal axis is such that the fingers (the first finger, the second finger, the third finger, and the little finger) side other than the thumb can be located in the second surface 18b and a dial 72 can be operated with, for example, the second finger when the operator locates the thumb of the hand grasping the endoscope body 12 in the fourth surface 18d.

The fifth surface 18e and the sixth surface 18f are respectively a distal-side surface and a proximal-side surface which extend from the first surface 18a, extend toward the axial direction of a rotation shaft 23 of the later-described UD curving operation knob 24, and are provided continuously with the third surface 18c. The fifth surface 18e and the sixth surface 18f may respectively intersect at right angles with the first to fourth surfaces 18a to 18d, or may be attached at a desired angle suitably to the member to be attached to the surfaces.

The operation portion body 18 has the UD curving operation knob 24 as a first curving operation portion which operates the curving of the curving portion 15 in the UD direction, an RL curving operation dial 27 as a second curving operation portion which operates the curving of the curving portion 15 in the RL direction, a rotation detection sensor 29, and an air/water switch (first switch) 33 and a suction switch (second switch) 34 as functional switches.

The UD curving operation knob 24 is provided in the first surface 18a of the operation portion body 18. The UD curving operation knob 24 is provided rotatably around the rotation shaft 23 protruding from the first surface 18a in the X-direction. The UD curving operation knob 24 is star-shaped and pentagonal, and has, for example, five claws. The operator rotates the UD curving operation knob 24 by putting the thumb of the hand grasping the endoscope body 12 on the claws.

FIG. 8 is a diagram schematically showing the mechanism of the endoscope body 12 regarding the UD curving operation of the curving portion 15. The proximal end of the UD curving operation wire 19 is wound around the turning drum 22 in the endoscope body 12 as described above. The rotation shaft 23 of the UD curving operation knob 24 is attached to the turning drum 22. Therefore, if the UD curving operation knob 24 is rotated, the turning drum 22 also rotates via the rotation shaft 23 and thus the UD curving operation wire 19 is moved, so that the curving portion 15 curves in the U-direction or the D-direction.

The RL curving operation dial 27 and the rotation detection sensor 29 are provided in the second surface 18b of the operation portion body 18. The RL curving operation dial 27 is a circular cylindrical rotor comprising a rotation shaft 28. The curving portion 15 curves in the R-direction or the L-direction by the rotation of the RL curving operation dial 27 around the rotation shaft 28.

FIG. 9 is a block diagram schematically showing control regarding the RL curving operation of the curving portion 15. The proximal end of the RL curving operation wire 20 is coupled to the driving force transmission section 25 as described above. The driving force transmission section 25 has a chain coupled to the proximal side of the RL curving operation wire 20 via a connection member, and a sprocket around which the chain is wound. The sprocket is coupled to an RL curving driving section 26. The RL curving driving section 26 has a wheel coaxially connected to the sprocket via a shaft, a gear which meshes with the wheel, and a motor coupled to the gear. The RL curving driving section 26 is connected to the control device 5 via the universal cord 13.

The rotation detection sensor 29 is coupled to the rotation shaft 28 of the RL curving operation dial 27. The rotation detection sensor 29 is a sensor to detect the rotation amount of the rotation shaft 28, and is, for example, a potentiometer. However, the rotation detection sensor 29 may be some other sensor (e.g. a rotary encoder) which can detect the rotation amount of the rotation shaft 28. The rotation detection sensor 29 reads the rotation angle, of the RL curving operation dial 27 via the rotation shaft 28 of the RL curving operation dial 27 to detect the rotation direction and rotation amount of the RL curving operation dial 27.

That is, if the RL curving operation dial 27 is rotated by the operator, the rotation direction and rotation amount input to the RL curving operation dial 27 are detected by the rotation detection sensor 29. An electric signal from the rotation detection sensor 29 is then output to the control device 5, and input to the RL curving driving section 26 from the control device 5. The RL curving driving section 26 is driven in response to this electric signal and then generates driving force to curve the curving portion 15 in the R-direction or the L-direction. This driving force is transmitted to the RL curving operation wire 20 via the driving force transmission section 25, and the RL curving operation wire 20 is moved accordingly. Thus, if the RL curving operation dial 27 is rotated, i.e., an instruction to curve the curving portion 15 in the R-direction or the L-direction is input to the RL curving operation dial 27, the curving portion 15 electrically curves in the R-direction or the L-direction.

Thus, in the endoscope 10, the curving portion 15 of the insertion portion 11 curves in the U-direction or the D-direction or in the R-direction or the L-direction independently of each other by the rotational operations of the UD curving operation knob 24 and the RL curving operation dial 27.

Regarding the operation of the curving portion 15 at the time of the insertion of the insertion portion 11 into the specimen, the curving operations in the UD direction and the RL direction are not equivalent in actuality. The main operation is the curving operation in the UD direction, and the curving operation in the RL direction is often used secondarily during an observation. Thus, in the present embodiment, the curving operation in the UD direction is performed by a manual operation mechanism, and the curving operation in the RL direction is electrically driven.

The first switch 33 and the second switch 34 are provided on a case 32 in the second surface 18b of the operation portion body 18. The first switch 33 and the second switch 34 are, for example, aligned in the longitudinal axis direction of the operation portion body 18. These switches 33 and 34 are pressed with the finger (e.g. the first finger or the second finger) other than the thumb of the operator grasping the endoscope body 12. The first switch 33 has, for example, a small hole made in its center. If the operator blocks this small hole with a finger, air is supplied via the air/water channel. If the switch is further pushed, water is supplied. If the second switch 34 is pushed, waterdrops and mucus adhering to the distal portion 14 of the insertion portion 11 are sucked and removed via the forceps channel.

The first switch 33 and the second switch 34 are examples of functional switches which are suitably operated to turn on predetermined functions of the endoscope, and other functions of the endoscope 10 may be allocated to these switches; for example, functions to take or enlarge an image of an observation target, and to switch photometry. The number of switches is not exclusively two, and one switch or three or more switches may be provided.

FIG. 10 is a diagram schematically showing the positional relation between the RL curving operation dial 27, the rotation shaft 28, the rotation detection sensor 29, and the second switch 34 provided in the second surface 18b of the operation portion body 18 in one aspect of the present embodiment.

In FIG. 10, two tangents of the suction switch (second switch) 34 parallel to the longitudinal axis direction of the operation portion body 18 are T1 and T2. The rotation shaft 28 of the RL curving operation dial 27 is disposed between the two tangents T1 and T2 closer to the distal side than the suction switch 34, that is, on the side of the grip portion 17 of the endoscope body 12. The region between the two tangents T1 and T2 is a range that is easily reached by the finger other than the thumb of the operator grasping the operation portion body 18.

The suction switch 34 is disposed at a position closer to the third surface 18c than the first surface 18a in the second surface 18b of the operation portion body 18. That is, the suction switch 34 and the RL curving operation dial 27 that is disposed between the two tangents are located close to the palm of the grasping hand when the operator grasps the operation portion body 18.

The RL curving operation dial 27 and the suction switch 34 are aligned in the longitudinal axis direction of the operation portion body 18.

In the present aspect, the RL curving operation dial 27 and the rotation detection sensor 29 are coupled to each other via the rotation shaft 28, and are therefore aligned in the longitudinal axis direction.

According to the present embodiment, the rotation axis of the RL curving operation dial is disposed between the two tangents T1 and T2 of the functional switch parallel to the longitudinal axis direction of the operation portion body 18, so that even if the operator has small hands or short fingers, the finger other than the thumb of the hand grasping the operation portion body 18, for example, the second finger easily reaches the RL curving operation dial 27. Thus, even a person with small hands or short fingers can easily perform a curving operation of the curving portion 15 in the RL direction only with one hand grasping the endoscope.

The functional switch is located closer to the third surface 18c than the first surface 18a in the second surface 18b of the operation portion body 18, so that the RL curving operation dial 27 disposed between the two tangents T1 and T2 of the functional switch is closer to the palm of the hand grasping the endoscope body 12. This arrangement is advantageous in that the finger more easily reaches the RL curving operation dial 27 even if the operator has small hands or short fingers.

For example, when the long insertion portion 11 comprising the curving portion on the distal side is inserted along the bending shape inside the specimen, the insertion portion 11 needs to be held with the hand (right hand) which is not grasping the operation portion body 18 to ensure the position of the insertion portion 11. Therefore, it is preferable to perform the curving operation of the curving portion 15 only with hand (right hand) grasping the operation portion body 18.

According to the present embodiment, the above-mentioned arrangement of the RL curving operation dial 27 enables the RL curving operation dial 27 to be easily operated with the finger other than the thumb of the grasping hand without the necessity of the aid of the hand which is not grasping the operation portion body 18 even if the operator has small hands or short fingers.

A diameter D27 of the RL curving operation dial 27 is smaller than a diameter D34 of the suction switch 34. A diameter D28 of the rotation shaft 28 is also smaller than the diameter D34 of the suction switch 34. Thus, the finger other than the thumb of the hand grasping the endoscope is put on the rotation shaft 28 of the RL curving operation dial 27, this finger easily reaches the UD curving operation knob 24 of the first surface 18a of the operation portion body 18. Therefore, the rotation operation of the UD curving operation knob 24 is easily assisted (e.g. fixed) with the finger other than the thumb of the grasping hand.

Figure 11:
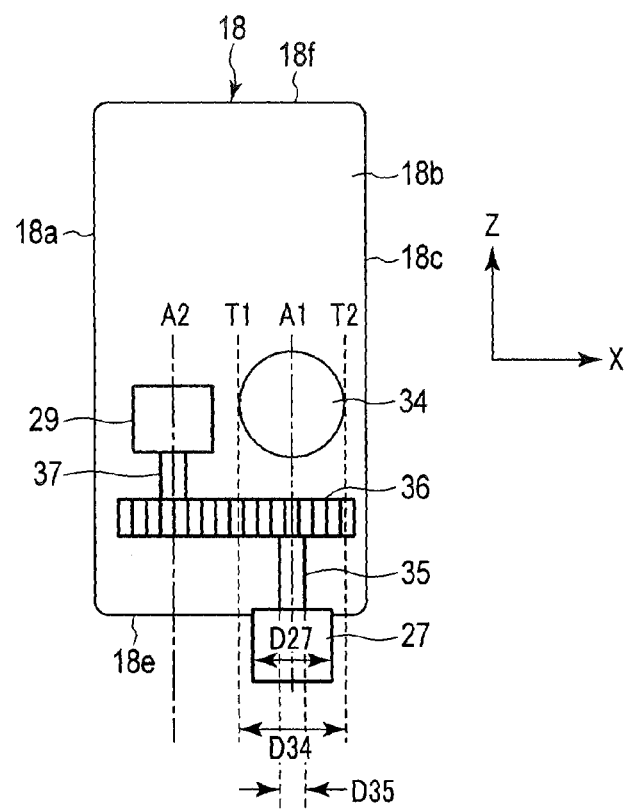
FIG. 11 is a diagram schematically showing another aspect of the positional relation between the switch and the RL operation dial in the operation portion body of the endoscope body.

FIG. 11 is a diagram schematically showing the positional relation between the RL curving operation dial 27, the rotation shaft 28, the rotation detection sensor 29, and the second switch 34 provided in the second surface 18b of the operation portion body 18 in another aspect of the present embodiment.

In the present aspect, the RL curving operation dial 27 and the rotation detection sensor 29 respectively have rotation shafts 35 and 37, and these are coupled to each other via a gear 36. That is, a center A1 of the rotation shaft 35 of the RL curving operation dial 27 and a center A2 of the rotation shaft 37 of the rotation detection sensor 29 are not aligned in the longitudinal axis direction, and are provided at different positions.

According to this arrangement, the location of the rotation detection sensor 29 has a degree of freedom, so that the position of the RL curving operation dial 27 in the longitudinal axis direction is not too close to the distal side of the operation portion body 18, and the finger of the operator can be located in an easily reachable range.

In the present aspect as well, the diameter D27 of the RL curving operation dial 27 is smaller than the diameter D34 of the suction switch 34. A diameter D35 of the rotation shaft 35 is also smaller than the diameter D34 of the suction switch 34. Thus, the finger other than the thumb of the hand grasping the endoscope easily reaches the UD curving operation knob 24 of the first surface 18a of the operation portion body 18.

Second Embodiment

The second embodiment of the present invention is described with reference to FIG. 12 to FIG. 17. Components similar to those in the first embodiment are indicated below with reference numbers in the hundreds corresponding to those in the first embodiment, and are not described.

Figure 12:
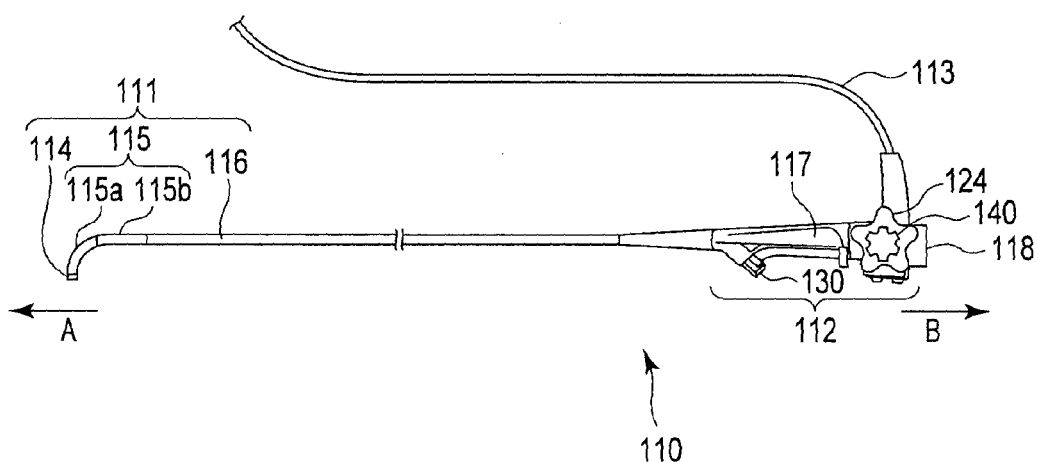
FIG. 12 is a diagram schematically showing an endoscope according to a second embodiment of the present invention.

FIG. 12 is a general view schematically showing an endoscope 110 according to a second embodiment. The endoscope 110 is similar to the endoscope 10 according to the first embodiment, and is a part of an endoscope apparatus having a light source device 2, a video processor device 3, an air/water supply device 4, a control device 5, an input keyboard 6, and a monitor 7.

The endoscope 110 in the present embodiment has a curving portion 115 composed of two curving portions that curve independently of each other to finely bend along the shape inside the specimen. That is, in the endoscope 110, the curving portion 115 of an insertion portion 111 has a distal-side first curving portion 115a and a proximal-side second curving portion 115b.

As in the first embodiment, a UD curving operation wire 119 for curving the first curving portion 115a in the UD direction as a first direction, and an RL curving operation wire 120 for curving the first curving portion 115a in the RL direction are inserted through the first curving portion 115a. A UD curving operation wire 149 for curving the second curving portion 115b in the UD direction as a second direction is inserted through the second curving portion 115b. Thus, in the present embodiment, both the first direction and the second direction are UD directions.

FIG. 13 to FIG. 15 are a front view, a top view, and a side view of an endoscope body 112, respectively. The operation portion body 118 has a UD curving operation knob 124 as a first curving operation portion which operates the curving of the first curving portion 115a in the UD direction, an RL curving operation knob 140 which operates the curving of the first curving portion 115a in the RL direction, a UD curving operation dial 141 as a second curving operation portion which operates the curving of the second curving portion 115b in the UD direction, a rotation detection sensor 129, and an air/water switch 133 and a suction switch 134 as functional switches.

The UD curving operation knob 124 is provided in a first surface 118a of the operation portion body 118. Moreover, the RL curving operation knob 140 is provided on the upper surface of the UD curving operation knob 124. The UD curving operation knob 124 and the RL curving operation knob 140 are provided rotatably around a rotation shaft 123 protruding in the X-direction. The RL curving operation knob 140 is star-shaped and hexagonal, and has, for example, six claws. The operator rotates the UD curving operation knob 124 or the RL curving operation knob 140 by putting the thumb of the hand grasping the endoscope body 112 on the claws of the UD curving operation knob 124 or the RL curving operation knob 140.

FIG. 16 is a diagram schematically showing the mechanism of the endoscope body 112 regarding the UD curving operation and RL curving operation of the first curving portion 115a. The proximal end of the UD curving operation wire 119 is wound around a turning drum 145 in the endoscope body 112. The rotation shaft of the UD curving operation knob 124 is attached to a rotation shaft 144 of the turning drum 145. Therefore, if the UD curving operation knob 124 is rotated, the turning drum 145 is also rotated via the rotation shaft 144 and thus the UD curving operation wire 119 is moved, so that the first curving portion 115a curves in the U-direction and the D-direction.

The proximal end of the RL curving operation wire 120 is wound around a turning drum 147 in the endoscope body 112. The rotation shaft of the RL curving operation knob 140 is attached to a rotation shaft 148 of the turning drum 147. Therefore, if the RL curving operation knob 140 is rotated, the turning drum 147 also rotates via the rotation shaft 148 and thus the RL curving operation wire 120 is moved, so that the first curving portion 115a curves in the R-direction and the L-direction.

In the present embodiment, a UD curving operation dial 143 and the rotation detection sensor 129 of the second curving portion 115b are provided in a second surface 118b of the operation portion body 118. The UD curving operation dial 141 is a circular cylindrical rotor comprising a rotation shaft 142. The second curving portion 115b electrically curves in the U-direction or the D-direction by the rotation of the UD curving operation dial 141 around the rotation shaft 142.

Figure 17:
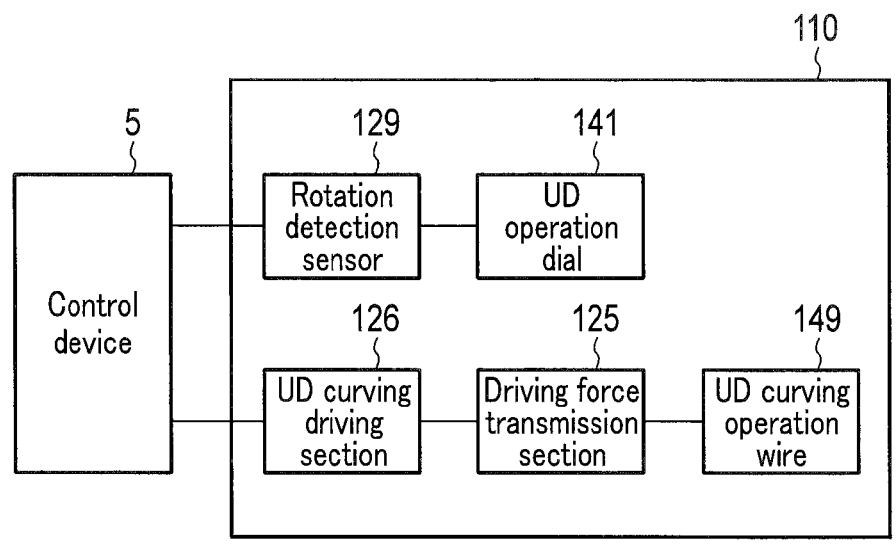
FIG. 17 is a block diagram schematically showing control regarding the UD curving operation of a second curving portion.

FIG. 17 is a block diagram schematically showing control regarding the UD curving operation of the second curving portion 115b. The proximal end of the UD curving operation wire 149 is coupled to a driving force transmission section 125. The driving force transmission section 125 has a chain coupled to the proximal side of the UD curving operation wire 149 via a connection member, and a sprocket around which the chain is wound. The sprocket is coupled to an UD curving driving portion 126. The UD curving driving portion 126 has a wheel coaxially connected to the sprocket via a shaft, a gear which meshes with the wheel, and a motor coupled to the gear. The UD curving driving portion 126 is connected to the control device 5 via a universal cord 113.

The rotation detection sensor 129 is coupled to the rotation shaft 142 of the UD curving operation dial 141. The rotation detection sensor 129 is a sensor to detect the rotation amount of the rotation shaft 142, and is, for example, a potentiometer or a rotary encoder. The rotation detection sensor 129 reads the rotation angle of the UD curving operation dial 143 via the rotation shaft 142 of the UD curving operation dial 141 to detect the rotation direction and rotation amount of the UD curving operation dial 141.

The UD curving operation dial 141 is rotated by the operator. The rotation direction and rotation amount input to the UD curving operation dial 141 are detected by the rotation detection sensor 129. If a curving operation signal indicating the curving operation in the UD direction is output to the control device 5, the control device 5 drives the UD curving driving portion 126 in accordance with the curving operation signal. The UD curving driving portion 126 then generates driving force to curve the second curving portion 115b in the UD direction, so that the UD curving operation wire 149 is moved via the driving force transmission section 125. Thus, if an instruction to curve the second curving portion 115b in the UD direction is input to the UD curving operation dial 141, the second curving portion 115b electrically curves in the U-direction or the D-direction.

An in the RL curving operation dial in the first embodiment, the rotation shaft 142 of the UD curving operation dial 141 is disposed between two tangents of the suction switch 134 closer to the distal side than the suction switch 134, that is, on the side of a grip portion of the endoscope body 112. The suction switch 134 is disposed at a position closer to a third surface 118c than the first surface 118a in the second surface 118b of the operation portion body 118. The UD curving operation dial 141 and the suction switch 134 are aligned in the longitudinal axis direction of the operation portion body 118.

In the present embodiment as well as in the first embodiment, the finger other than the thumb of the hand grasping the operation portion body 118 easily reaches the UD curving dial even in the case of an operator with small hands or an operator with short fingers. Thus, even a person with small hands or short fingers can easily perform a curving operation of the second curving portion in the UD direction only with one hand grasping the endoscope.

Third Embodiment

The third embodiment of the present invention is described with reference to FIG. 18 to FIG. 21. Components similar to those in the first embodiment are indicated below with reference numbers in the two hundreds corresponding to those in the first embodiment, and are not described.

Figure 18:
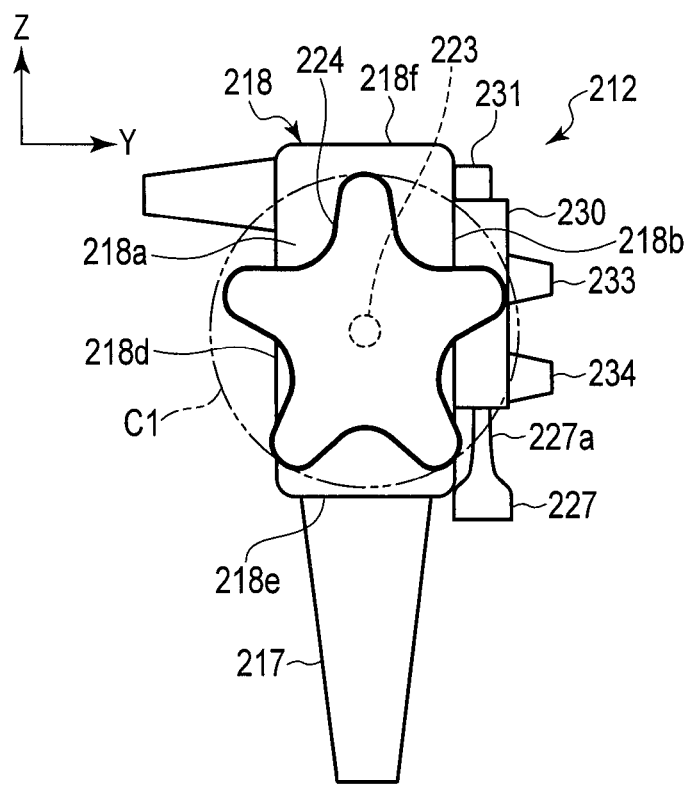
FIG. 18 is a front view of the endoscope body in the YZ plane according to a third embodiment of the present invention.
Figure 21:
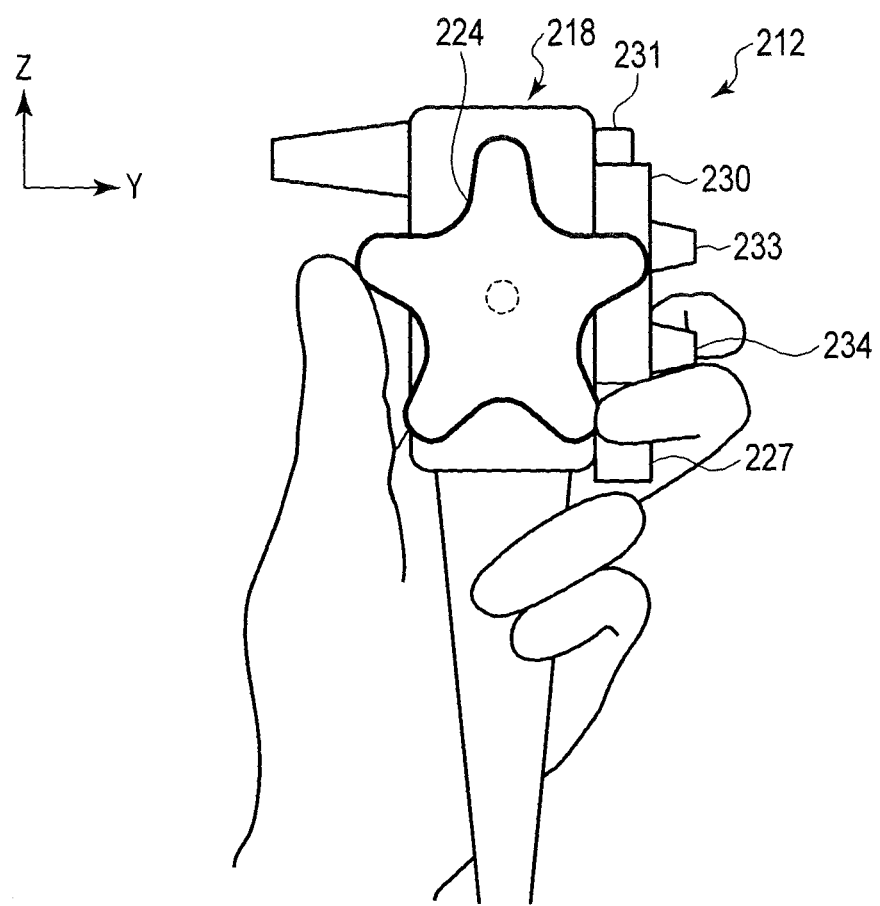
FIG. 21 is a front view in the YZ plane in which the operator is grasping the endoscope body.

FIG. 18 to FIG. 20 are a front view, a top view, and a side view of an endoscope body 212, respectively. FIG. 21 is a front view in which the operator is grasping the endoscope body 212. In FIG. 18 to FIG. 21, an X-direction, a Y-direction, and a Z-direction are defined as in FIG. 4 to FIG. 7. An operation portion body 218 has first to sixth surfaces 218a to 218f similar to those in the first embodiment.

The operation portion body 218 has a UD curving operation knob 224 as a first rotor which operates the curving of a curving portion 215 in the UD direction, an RL curving operation dial 227 as a second rotor which operates the curving of the curving portion 215 in the RL direction, a rotation detection sensor 229 housed in a dial case 230, an imaging switch 231, and an air/water switch 233 and a suction switch 234 as functional switches.

The UD curving operation knob 224 is provided in the first surface 218a of the operation portion body 218. The UD curving operation knob 224 is provided rotatably around a rotation shaft 223 protruding from the first surface 218a in the X-direction. The UD curving operation knob 224 is star-shaped and pentagonal, and has, for example, five claws. The operator rotates the UD curving operation knob 224 by putting the thumb of the hand grasping the endoscope body 212 on the claws.

The RL curving operation dial 227 and the dial case 230 which houses the rotation detection sensor 229 are provided on the side of the first surface 218a (at the position close to the first surface 218a) in the second surface 218b of the operation portion body 218. The RL curving operation dial 227 is a rotor comprising a rotation shaft, and extends from the dial case 230 to the distal side of the operation portion body 218. The curving portion 215 electrically curves in the R-direction or the L-direction by the rotation of the RL curving operation dial 227 around the rotation shaft.

The rotation detection sensor 229 is coupled to the rotation shaft of the RL curving operation dial 227. The rotation detection sensor 229 is a sensor to detect the rotation amount of the RL curving operation dial 227, and is, for example, a potentiometer. However, the rotation detection sensor 229 may be some other sensor (e.g. a rotary encoder) which can detect the rotation amount of the RL curving operation dial 227. The rotation detection sensor 229 reads the rotation angle of the RL curving operation dial 227 via the rotation shaft of the RL curving operation dial 227 to detect the rotation direction and rotation amount of the RL curving operation dial 227.

That is, if the RL curving operation dial 227 is rotated by the operator, the rotation direction and rotation amount input to the RL curving operation dial 227 are detected by the rotation detection sensor 229. An electric signal from the rotation detection sensor 229 is then output to the control device 5, and input to an RL curving driving section 226 from the control device 5. The RL curving driving section 226 is driven in response to this electric signal and then generates driving force to curve the curving portion 215 in the R-direction or the L-direction. This driving force is transmitted to an RL curving operation wire 220 via a driving force transmission section 225, and the RL curving operation wire 220 is moved accordingly. If the RL curving operation dial 227 is rotated, i.e., an instruction to curve the curving portion 215 in the R-direction or the L-direction is input to the RL curving operation dial 227, the curving portion 215 electrically curves in the R-direction or the L-direction.

Thus, in an endoscope 210, the curving portion 215 of an insertion portion 211 curves in the U-direction or the D-direction or in the R-direction or the L-direction independently of each other by the rotational operations of the UD curving operation knob 224 and the RL curving operation dial 227.

The imaging switch 231 is provided on the side of the third surface 218c in the second surface 218b of the operation portion body 218. The imaging switch is 231 is a switch to control the on/off of imaging by, for example, an observation optical system at a distal end 214. The air/water switch 233 and the suction switch 234 are provided on a base 232 in the second surface 218b of the operation portion body 218 on the side of the third surface 218c (at the position close to the third surface 218c). Thus, the base 232 is a mounting surface for the switches 233 and 234. The air/water switch 233 and the suction switch 234 are switches to control the on/off of the supply of air/water or suction to an air/water channel for lens cleaning or for the suction of liquids and tissues in the specimen. These switches 231, 233, and 234 are pressed and operated with the finger (e.g. the first finger or the second finger) other than the thumb of the operator grasping the endoscope body 212.

These switches 231, 233, and 234 are examples of functional switches which are suitably operated to turn on predetermined functions of the endoscope, and other functions of the endoscope 210 may be allocated to these switches; for example, functions to enlarge an image of an observation target, and to switch photometry. The number of switches is not exclusively the above, and one or two switches or four or more switches may be provided.

In the present embodiment, as best shown in FIG. 20, a recess 227a which is recessed toward the rotation axis of the RL curving operation dial 227 is provided in the RL curving operation dial 227. The recess 227a is provided between a distalmost position L232 of the base 232 or a distalmost position L234 of the suction switch 234 and a distalmost position L227 of the RL curving operation dial 227 in the Z-direction.

The recess 227a is provided so that the distalmost position L232 of the base 232 or the distalmost position L234 of the suction switch 234 is located inside an outer circumferential circle C1 (shown in FIG. 17) of the UD curving operation knob 224 in the Z-direction. That is, in the Z-direction, the distalmost position L232 of the base 232 or the distalmost position L234 of the suction switch 234 is located closer to the proximal side than a distalmost position L224 of the UD curving operation knob 224.

Furthermore, the recess 227a is provided so that the region between the distalmost position L232 of the base 232 or the distalmost position L234 of the suction switch 234 and the distalmost position L227 of the RL curving operation dial 227 overlaps the region inside the outer circumferential circle C1 of the UD curving operation knob 224 in the Z-direction. That is, in the Z-direction, the distalmost position L224 of the UD curving operation knob 224 is located between the distalmost position L232 of the base 232 or the distalmost position L234 of the suction switch 234 and the distalmost position L227 of the RL curving operation dial 227.

When the curving portion 215 is curved, normally, the UD curving operation knob 224 is operated with the thumb of the hand grasping the endoscope body 212, and the RL curving operation dial 227 is operated with the finger other than the thumb. For example, when the UD curving operation knob 224 is fixed, the operation of the UD curving operation knob 224 needs to be assisted by the finger (normally, the second finger or the third finger) other than the thumb. In this case, in the endoscope in which the whole RL curving operation dial 227 is exposed outside the operation portion body 218 in the range where the finger other than the thumb of the hand grasping the endoscope body 212 is put, the finger to reach the UD curving operation knob 224 is blocked by the RL curving operation dial 227, so that it is difficult for this finger to reach the UD curving operation knob 224.

According to the present embodiment, a recess 228 is provided in the RL curving operation dial 227 between the distalmost position of the base 232 which is the mounting surface for the functional switches and the distalmost position of the UD curving operation knob 224. Thus, even in the endoscope 210 in which the whole RL curving operation dial 227 is exposed outside the operation portion body 218, the RL curving operation dial 227 does not block the action of the finger other than the thumb to extend to the first surface 218a from the second surface 218b of the operation portion body 218. Therefore, the finger other than the thumb easily reaches the UD curving operation knob 224, and the assist operation for the UD curving operation knob 224 is easily performed.

In the longitudinal axis direction, the distalmost position of the base is closer to the distal side than the distalmost position of the UD curving operation knob 224. Thus, in the second surface 218b of the operation portion, body 218, it is possible to secure a route passing over the recess 228 for the finger other than the thumb grasping the endoscope 210 to access the UD curving operation knob 224 of the first surface 218a.

Furthermore, in the longitudinal axis direction, the distalmost position of the UD curving operation knob 224 is located between the distalmost position of the base and the RL curving operation dial 227. Thus, for example, the recess 228 can be recessed over the width equal to or more than the width of the finger to extend to the UD curving operation knob 224, and an accessible route passing over the recess 228 can be secured.

In the present embodiment, the recess 228 is provided in the RL curving operation dial 227 to maintain a diameter suitable to the operation of the RL curving operation dial 227 having a resolving power that can finely set the curving amount of the curving portion 215 and to reduce the distance from the RL curving operation dial 227 to the UD curving operation knob 224 at the same time. Therefore, it is possible to maintain performance similar to the performance of a conventional electrically curving endoscope.

Fourth Embodiment

The fourth embodiment of the present invention is described with reference to FIG. 22 to FIG. 24. Components similar to those in the second embodiment are indicated below with reference numbers in the three hundreds corresponding to those in the second or third embodiment, and are not described.

An endoscope 310 in the present embodiment has a curving portion 115 composed of two curving portions that independently curve to finely bend along the shape inside the specimen, as in the second embodiment. That is, in the endoscope 310, the curving portion 115 of an insertion portion 111 has a distal-side first curving portion 115a and a proximal-side second curving portion 115b.

FIG. 22 to FIG. 24 are a front view, a top view, and a side view of an endoscope body 312, respectively. An operation portion body 318 has a UD curving operation knob 324 which is a first rotor to operate the curving of the first curving portion 115a in the UD direction, an RL curving operation knob 340 which operates the curving of the first curving portion 115a in the RL direction, a UD curving operation dial 327 which is a second rotor to operate the curving of the second curving portion 115b in the UD direction, a dial case 330 which houses a rotation detection sensor 329, an imaging switch 331, and an air/water switch 333 and a suction switch 334 which are functional switches.

The UD curving operation knob 324 is provided in a first surface 318a of the operation portion body 318. Moreover, the RL curving operation knob 340 is provided on the upper surface of the UD curving operation knob 324. The UD curving operation knob 324 and the RL curving operation knob 340 are provided rotatably around a rotation shaft 323 protruding in the X-direction. The RL curving operation knob 340 is star-shaped and hexagonal, and has, for example, six claws. The operator rotates the UD curving operation knob 324 or the RL curving operation knob 340 by putting the thumb of the hand grasping the endoscope body 312 on the claws of the UD curving operation knob 324 or the RL curving operation knob 340.

In the present embodiment, the UD curving operation dial 327 of the second curving portion 115b and the dial case 330 which houses the rotation detection sensor 329 are provided in a second surface 318b of the operation portion body 318 on the side of the first surface 318a (at the position close to the first surface 318a). The UD curving operation dial 327 is a rotor comprising a rotation shaft, and extends from the dial case 330 to the distal side of the operation portion body 318. The second curving portion 115b electrically curves the U-direction or the D-direction by the rotation of the UD curving operation dial 327 around the rotation shaft.

The rotation detection sensor 329 is coupled to the rotation shaft of the UD curving operation dial 327. The rotation detection sensor 329 is a sensor to detect the rotation amount of the rotation shaft, and is, for example, a potentiometer or a rotary encoder. The rotation detection sensor 329 reads the rotation angle of the UD curving operation dial 327 via the rotation shaft of the UD curving operation dial 327 to detect the rotation direction and rotation amount of the UD curving operation dial 327.

The UD curving operation dial 327 is rotated by the operator. The rotation direction and rotation amount input to the UD curving operation dial 327 are detected by the rotation detection sensor 329. If a curving operation signal indicating the curving operation in the UD direction is output to the control device 5, the control device 5 drives a UD curving driving portion 326 in accordance with the curving operation signal. The UD curving driving portion 326 then generates driving force to curve the second curving portion 115b in the UD direction, so that a UD curving operation wire 349 is moved via a driving force transmission section 325. Thus, if an instruction to curve the second curving portion 115b in the UD direction is input to the UD curving operation dial 327, the second curving portion 115b electrically curves in the U-direction or the D-direction.

In the present embodiment as well, as best shown in FIG. 24, a recess 327a which is recessed toward the rotation axis of the UD curving operation dial 327 is provided in the UD curving operation dial 327. The recess 327a is provided between a distalmost position L332 of a base 332 or a distalmost position L334 of the suction switch 334 and a distalmost position L327 of the UD curving operation dial 327 in the Z-direction.

The recess 327a is provided so that the distalmost position L332 of the base 332 or the distalmost position L334 of the suction switch 334 is located inside an outer circumferential circle C1 (shown in FIG. 18) of the UD curving operation knob 324 in the Z-direction. Further, the recess 327a is provided so that the region between the distalmost position L332 of the base 332 or the distalmost position L334 of the suction switch 334 and the distalmost position L327 of the UD curving operation dial 327 overlaps the region inside the outer circumferential circle C1 of the UD curving operation knob 324 in the Z-direction.

In the present embodiment as well, the recess 327a is provided in the UD curving operation dial 327, so that the UD curving operation dial 327 does not block the action of the finger other than the thumb of the hand grasping the endoscope body 312 to extend to the first surface 318a from the second surface 318b of the operation portion body 318. Therefore, the finger other than the thumb easily reaches the UD curving operation knob 324, and the assist operation for the UD curving operation knob 324 is easily performed. Moreover, it is possible to secure a route in which the finger other than the thumb of the hand grasping the endoscope 310 easily accesses the UD curving operation knob 324 by setting the distalmost positions of the base 332, the UD curving operation knob 324, the suction switch 334, and the UD curving operation dial 327 as described above.

While the first to fourth embodiments of the present invention have been described above, the present invention is not limited to the embodiments described above, and it will occur to those skilled in the art that various improvements and modifications can be made without departing from the spirit of the present invention.

Although the endoscope having the observation optical system and the illumination optical system has been described as an example of the insertion instrument, the insertion instrument also includes insertion instruments which do no have the above optical systems.

Fifth Embodiment

Figure 25:
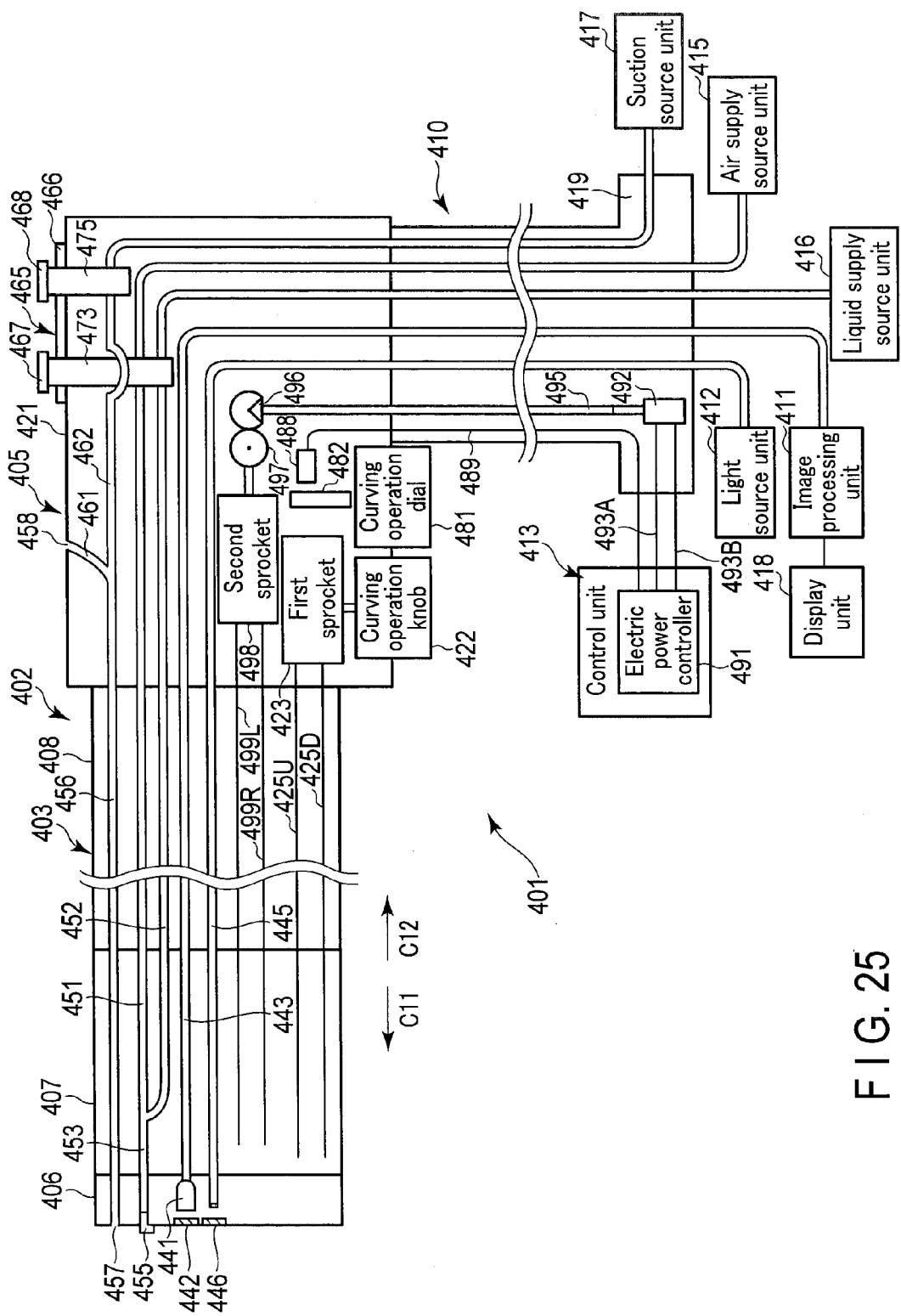
FIG. 25 is a schematic diagram showing an endoscope apparatus according to a fifth embodiment of the present invention.

The fifth embodiment of the present invention is described with reference to FIG. 25 to FIG. 32. FIG. 25 is a diagram showing an endoscope apparatus 401 which is an insertion apparatus according to the fifth embodiment. As shown in FIG. 25, the endoscope apparatus 401 comprises an endoscope 402 as the insertion apparatus. FIG. 26 is a diagram showing the configuration of the endoscope 402. As shown in FIG. 26, the endoscope 402 has a longitudinal axis C. Here, one of directions parallel to the longitudinal axis C is a distal direction (a direction of an arrow C11 in FIG. 26), and a direction opposite to the distal direction is a proximal direction (a direction of an arrow C12 in FIG. 26). The distal direction and the proximal direction are longitudinal axis directions parallel to the longitudinal axis C. The endoscope 402 comprises an insertion portion 403 extending from the proximal direction to the distal direction along the longitudinal axis C, and a holding portion 405 provided on the proximal direction side of the insertion portion 403.

The insertion portion 403 comprises a distal rigid portion 406 which forms the distal end of the insertion portion 403, a curving portion 407 provided on the proximal direction side of the distal rigid portion 406, and a flexible tube 408 provided on the proximal direction side of the curving portion 407. The curving portion 407 can curve in a U-direction (a direction of an arrow U in FIG. 26, hereinafter referred to as a U-direction) and in a curving-DOWN-direction (a direction of an arrow D in FIG. 26, hereinafter referred to as a D-direction) opposite to the U-direction. The curving portion 407 can also curve in a curving-LEFT-direction (a direction of an arrow L in FIG. 26, hereinafter referred to as an L-direction) and in a curving-RIGHT-direction (a direction of an arrow R in FIG. 26, hereinafter referred to as an R-direction) opposite to the L-direction. Here, in the present embodiment, the UD directions are first curving directions which are two directions perpendicular to the longitudinal axis C. The LR directions are second curving directions which are two directions perpendicular to the first perpendicular direction. The curving portion 407 curves in the first curving directions (UD directions) as a first action, and curves in the second curving directions (LR directions) as a second action. Therefore, the curving portion 407 serves as an action portion which performs the first action and the second action different from the first action.

One end of a universal cord 410 is connected to the holding portion 405. A scope connector 419 is provided at the other end of the universal cord 410. As shown in FIG. 25, the endoscope apparatus 401 comprises an image processing unit 411, a light source unit 412, a control unit 413, an air supply source unit 415, a liquid supply source unit 416, a suction source unit 417, and a display unit 418 such as a monitor. The holding portion 405 is connected to the image processing unit 411, the light source unit 412, the control unit 413, the air supply source unit 415, the liquid supply source unit 416, and the suction source unit 417 via the universal cord 410. The display unit 418 is electrically connected to the image processing unit 411.

FIG. 27 to FIG. 29 are diagrams showing the configuration of the holding portion 405. As shown in FIG. 26 to FIG. 29, the holding portion 405 comprises a holding portion casing 421, and a curving operation knob 422 which is rotatable relative to the holding portion casing 421 around a rotation axis P11. The rotation axis P11 extends in a direction different from the longitudinal axis C. For example, the rotation axis P11 is substantially perpendicular to the longitudinal axis C. A first operation to operate the curving of the curving portion 407 in the first curving directions is input by the rotation of the curving operation knob 422 around the rotation axis P11. That is, the curving operation knob 422 serves as a first operation input portion to which the first operation to operate the first action of the curving portion (action portion) 407 is input. Driving force for the first action of the curving portion 407 which is the action portion is generated by the rotation of the curving operation knob 422 which is the first operation input portion. The outer circumferential portion of the curving operation knob 422 is formed into a protruding and recessed shape along a direction around the rotation axis. Here, the rotation axis P11 is substantially perpendicular to the longitudinal axis C, which shows that the rotation axis P11 does not need to be strictly perpendicular to the longitudinal axis C, and a slight difference resulting from, for example, designing is permitted.

As shown in FIG. 25, a first sprocket 423 is provided inside the light source unit 412. The first sprocket 423 is coupled to the curving operation knob 422, and the first sprocket 423 rotates by the input of a curving operation in the curving operation knob 422. Two first curving wires 425U and 425D extend along the longitudinal axis C inside the insertion portion 403. The proximal ends of the first curving wires 425U and 425D are connected to the first sprocket 423. The distal ends of the first curving wires 425U and 425D are connected to the distal end of the curving portion 407. One of the first curving wires 425U and 425D is pulled in the proximal direction by the rotation of the first sprocket 423. The curving portion 407 curves in the U-direction in response to the puling of the first curving wire 425U. The curving portion 407 curves in the D-direction in response to the puling of the first curving wire 425D.

Here, one of directions parallel to the rotation axis P11 is a first rotation axis direction (a direction of an arrow T11 in FIG. 26, FIG. 28, and FIG. 29), and a direction opposite to the first rotation axis direction is a second rotation axis direction (a direction of an arrow T12 in FIG. 26, FIG. 28, and FIG. 29). One of directions perpendicular to the longitudinal axis C and perpendicular to the rotation axis P11 is a first perpendicular direction (a direction of an arrow Q11 in FIG. 26, FIG. 27, and FIG. 29), and a direction opposite to the first perpendicular direction is a second perpendicular direction (a direction of an arrow Q12 in FIG. 26, FIG. 27, and FIG. 29). When the first rotation axis direction is the forward direction for the operator, the first perpendicular direction is a leftward direction, and the second perpendicular direction is a rightward direction. FIG. 27 is a diagram in which the holding portion 405 is seen from the first rotation axis direction side. FIG. 28 is a diagram in which the holding portion 405 is seen from the first perpendicular direction side. FIG. 29 is a diagram in which the holding portion 405 is seen from the proximal direction side.

As shown in FIG. 27 to FIG. 29, the holding portion casing 421 comprises a first casing outer surface 431 facing in the first rotation axis direction, and a second casing outer surface 432 facing in the first perpendicular direction. The curving operation knob 422 which is the first operation input portion is disposed in the first casing outer surface 431. The holding portion casing 421 also comprises a third casing outer surface 433 facing in the second rotation axis direction, a fourth casing outer surface 435 facing in the second perpendicular direction, and a fifth casing outer surface 437 facing in the proximal direction. The universal cord 410 is connected to the holding portion casing 421 from the second perpendicular direction side.

As shown in FIG. 25, an image pickup device 441 such as a CCD is provided inside the distal rigid portion 406. The image pickup device 441 images a subject through an observation window 442 provided in the distal surface of the insertion portion 403. One end of an imaging cable 443 is connected to the image pickup device 441. The imaging cable 443 extends through the insertion portion 403, the holding portion 405, and the universal cord 410. The other end of the imaging cable 443 is connected to the image processing unit 411. A subject figure imaged by the image processing unit 411 is subjected to image processing by the image processing unit 411, and displayed on the display unit 418.

A light guide 445 extends through the insertion portion 403 along the longitudinal axis C. One end of the light guide 445 is optically connected to an illumination window 446 provide in the distal surface of the insertion portion 403. The light guide 445 extends through the insertion portion 403, the holding portion 405, and the universal cord 410. The other end of the light guide 445 is connected to the light source unit 412. Light emitted from the light source unit 412 is applied to the subject from the illumination window 446 through the light guide 445.

An air supply path 451 and a liquid supply path 452 extend through the insertion portion 403 along the longitudinal axis C. The air supply path 451 and the liquid supply path 452 join at the distal end of the insertion portion 403, and form a joint path 453. A nozzle 455 is provided in the distal surface of the insertion portion 403. The air (fluid) supplied to the distal direction through the air supply path 451 and the liquid (fluid) supplied to the distal direction through the liquid supply path 452 are emitted from the nozzle 455 through the joint path 453. The air supply path 451 and the liquid supply path 452 extend through the insertion portion 403, the holding portion 405 (the holding portion casing 421), and the universal cord 410. The air supply path 451 is connected to the air supply source unit 415, and the liquid supply path 452 is connected to the liquid supply source unit 416.

A treatment instrument channel 456 extends through the insertion portion 403 along the longitudinal axis C. The treatment instrument channel 456 is open to the outside through a distal opening 457 provided in the distal surface of the insertion portion 403. The treatment instrument channel 456 extends into the holding portion 405 through the insertion portion 403. The treatment instrument channel 456 branches into a treatment instrument insertion hole 461 and a suction path 462 inside the holding portion 405. As shown in FIG. 26, a treatment instrument insertion opening 458 is formed in the second casing outer surface 432 of the holding portion casing 421. The treatment instrument insertion hole 461 is open to the outside of the holding portion casing 421 through the treatment instrument insertion opening 458. The suction path 462 extends through the holding portion 405 (the holding portion casing 421) and the universal cord 410. The suction path 462 is connected to the suction source unit 417.

As shown in FIG. 27 to FIG. 29, a button unit 465 is disposed in the second casing outer surface 432 of the holding portion casing 421. The button unit 465 comprises a button substrate 466, and an air/liquid operation button (first button) 467 and a suction operation button (second button) 468 attached to the button substrate 466. In the longitudinal axis direction parallel to the longitudinal axis C, the position of the button unit 465 substantially corresponds to the position of the curving operation knob 422. In the second casing outer surface 432, the button unit 465 is located in a part on the first rotation axis direction side. Therefore, the button unit 465 is provided parallel to the second rotation axis direction side of the curving operation knob 422.

The first button 467 and the second button 468 protrude toward the first perpendicular direction from the button substrate 466. A first press surface 471 is provided in the first button 467, and a second press surface 472 is provided in the second button 468. The first press surface 471 and the second press surface 472 face in the first perpendicular direction. The air supply path 451, the liquid supply path 452, and the suction path 462 pass in the vicinity of the button unit 465 inside the holding portion casing 421.

As shown in FIG. 25, an air/liquid supply valve 473 is provided inside the holding portion casing 421 in the vicinity of the button unit 465. The air/liquid supply valve 473 is disposed in the air supply path 451 and the liquid supply path 452. A switch operation to switch the open/close state in the air supply path 451 by the air/liquid supply valve 473 and the open/close state in the liquid supply path 452 by the air/liquid supply valve 473 is input by the air/liquid operation button 467. That is, the actuation state of the air/liquid supply valve 473 which is a functional unit is switched by the first button 467. In the switch operation of the air/liquid supply valve 473, the first press surface 471 of the first button 467 is pressed in the second perpendicular direction.

As a result, the air/liquid operation button 467 moves relative to the button substrate 466 in the second perpendicular direction. The first press surface 471 of the first button 467 is then pressed up to a switch position so that the open/close state in the air supply path 451 and the open/close state in the liquid supply path 452 are switched.

A suction valve 475 is provided inside the holding portion casing 421 in the vicinity of the button unit 465. The suction valve 475 is disposed in the suction path 462. A switch operation to switch the open/close state in the suction path 462 by the suction valve 475 is input by the second button 468. That is, the actuation state of the suction valve 475 which is a functional unit is switched by the second button 468. In the switch operation of the suction valve 475, the second press surface 472 of the second button 468 is pressed in the second perpendicular direction. As a result, the second button 468 moves relative to the button substrate 466 in the second perpendicular direction. The second press surface 472 of the second button 468 is then pressed up to a switch position so that the open/close state in the suction path 462 is switched. The air/liquid supply valve 473 and the suction valve 475 are functional units provided separately from the curving portion 407 which is the action portion.

As shown in FIG. 27 and FIG. 28, a step portion 477 is provided on the button substrate 466 of the button unit 465. The distal end of the button unit 465 is formed by the step portion 477. In the second casing outer surface 432, steps in the first perpendicular direction and the second perpendicular direction are formed by the step portion 477. Owing to the step portion 477, the button unit 465 (button substrate 466) protrudes in the first perpendicular direction in the second casing outer surface 432. Here, a rotation locus where the outer circumferential end of the curving operation knob 422 passes by rotation is an outermost circumferential locus S0. The step portion 477 is located closer to the proximal direction side than the distal end of the outermost circumferential locus S0.

A curving operation dial 481 is disposed in the second casing outer surface 432 of the holding portion casing 421. The curving operation dial 481 is rotatable around a drive axis P12. The drive axis P12 extends toward the proximal direction side from the curving operation dial 481 in such a manner as to cross over the rotation axis P11 of the curving operation knob 422 (at a skew position). The drive axis P12 may be parallel to the longitudinal axis C, and does not need to be parallel to the longitudinal axis C. A second operation to operate the curving of the curving portion 407 in the second curving directions is input by the rotation of the curving operation dial 481 around the drive axis P12. That is, the curving operation dial 481 serves as a second operation input portion to which the second operation to operate the second action of the curving portion (action portion) 407 is input. The curving operation dial 481 is located closer to the second rotation axis direction side than the button unit 465. The curving operation dial 481 is located closer to the distal direction side than the distal end of the outermost circumferential locus S0 of the curving operation knob 422.

A shaft portion 482 is coupled to the proximal direction side of the curving operation dial 481. The shaft portion 482 extends toward the proximal direction side from the curving operation dial 481 along the drive axis P12 which crosses over the rotation axis P11. The shaft portion 482 comprises a shaft fixing portion 483 which is fixed to the holding portion casing 421, and a shaft rotation portion 485 rotatable around the drive axis P12. The second operation is input by the rotation of the curving operation dial 481, and the shaft rotation portion 485 rotates around the drive axis P12 accordingly.

A housing portion formation surface 487 for forming a housing portion 486 for the insertion of the shaft portion 482 inside the holding portion casing 421 is provided in the second casing outer surface 432. The housing portion formation surface 487 is provided to protrude in the first perpendicular direction. The housing portion 486 is formed to be provided parallel to the second rotation axis direction side of the button unit 465. Thus, the housing portion formation surface 487 is provided parallel to the second rotation axis direction side of the button unit 465, and located in the part on the second rotation axis direction side in the second casing outer surface 432. As described above, inside the holding portion casing 421, the air supply path 451, the liquid supply path 452, and the suction path 462 pass through the region located in the vicinity of the button unit 465. The housing portion 486 (the housing portion formation surface 487) is configured to be provided parallel to the second rotation axis direction side of the button unit 465, so that a space having a size sufficient to form the housing portion 486 is secured inside the holding portion casing 421 in the region located on the second rotation axis direction side in the vicinity of the button unit 465.

As shown in FIG. 25, a rotation sensor 488 which detects the rotation state of the shaft rotation portion 485 is provided inside the holding portion casing 421. The rotation sensor 488 is located in the housing portion 486. One end of an electric signal line 489 is connected to the rotation sensor 488. The electric signal line 489 extends through the holding portion 405 (the holding portion casing 421) and the universal cord 410. The control unit 413 comprises an electric power controller 491. The other end of the electric signal line 489 is connected to the electric power controller 491. Information regarding the rotation state of the shaft rotation portion 485 detected by the rotation sensor 488 is transmitted to the electric power controller 491 via the electric signal line 489. The rotation state of the shaft rotation portion 485 changes in response to the second operation in the curving operation dial 481. Therefore, information regarding the second operation is detected in the electric power controller 491 by the transmission of the information regarding the rotation state of the shaft rotation portion 485.

An electric motor 492 which is a driving source is provided inside the electric power controller 491 of the universal cord 410. One end of each of electric wiring lines 493A and 493B is connected to the electric motor 492. The other end of each of the electric wiring lines 493A and 493B is connected to the electric power controller 491 of the control unit 413. When electric power is supplied to the electric motor 492 from the electric power controller 491, the electric motor 492 is driven, and driving force for the second action of the curving portion 407 which is the action portion is generated.

A driving shaft 495 extends through the universal cord 410. One end of the driving shaft 495 is connected to the electric motor 492. A bevel gear 496, and a spur gear 497 which meshes with the bevel gear 496 are provided inside the holding portion casing 421. A second sprocket 498 rotatable together with the spur gear 497 is also provided inside the holding portion casing 421. The other end of the driving shaft 495 is connected to the bevel gear 496. The driving force for the second action generated in the electric motor 492 is transmitted to the second sprocket 498 via the driving shaft 495, the bevel gear 496, and the spur gear 497.

The second sprocket 498 then rotates by the transmission of the driving force for the second action.

Two second curving wires 499L and 499R extend through the insertion portion 403 along the longitudinal axis C. The proximal ends of the second curving wires 499L and 499R are connected to the second sprocket 498. The distal ends of the second curving wires 499L and 499R are connected to the distal end of the curving portion 407. One end of each of the second curving wires 499L and 499R is pulled to the proximal direction by the rotation of the second sprocket 498. When the second curving wire 499L is pulled, the curving portion 407 curves in the L-direction. When the second curving wire 499R is pulled, the curving portion 407 curves in the R-direction.

FIG. 30 is a diagram showing the configurations of the button unit 465 and the housing portion formation surface 487. FIG. 30 is a view from the first rotation axis direction side. In FIG. 30, the first button 467 and the second button 468 located at the switch positions are indicated by solid lines, and the first button 467 and the second button 468 located at the unpressed positions where these buttons are not pressed to the second perpendicular direction are indicated by dotted lines. As described above, if the first button 467 is pressed to the switch position in the second perpendicular direction, the actuation state of the air/liquid supply valve 473 which is a functional unit is switched. Similarly, if the second button 468 is pressed to the switch position in the second perpendicular direction, the actuation state of the suction valve 475 which is a functional unit is switched. As shown in FIG. 30, when the first button 467 is located at the switch position, the first press surface 471 of the first button 467 protrudes toward the first perpendicular direction side from the housing portion formation surface 487. Similarly, when the second button 468 is located at the switch position, the second press surface 472 of the second button 468 protrudes toward the first perpendicular direction side from the housing portion formation surface 487.

As shown in FIG. 27 to FIG. 29, the housing portion 486 is open to the outside of the holding portion casing 421 through an opening 501. The opening 501 is located closer to the distal direction side than the step portion 477 of the button unit 465. The shaft portion 482 comprises a shaft exposing portion 502 protrudes toward the distal direction side from the distal direction side through the opening 501. The shaft exposing portion 502 is exposed to the outside of the holding portion casing 421 in the second casing outer surface 432. The shaft exposing portion 502 comprises a shaft recess 503 which is recessed toward the second perpendicular direction. The shaft recess 503 is always recessed toward the second perpendicular direction regardless of the rotation state of the shaft rotation portion 485. The shaft recess 503 is located between the step portion 477 of the button unit 465 and the distal end of the outermost circumferential locus S0 of the curving operation knob 422 in the longitudinal axis direction parallel to the longitudinal axis C.

Figure 32:
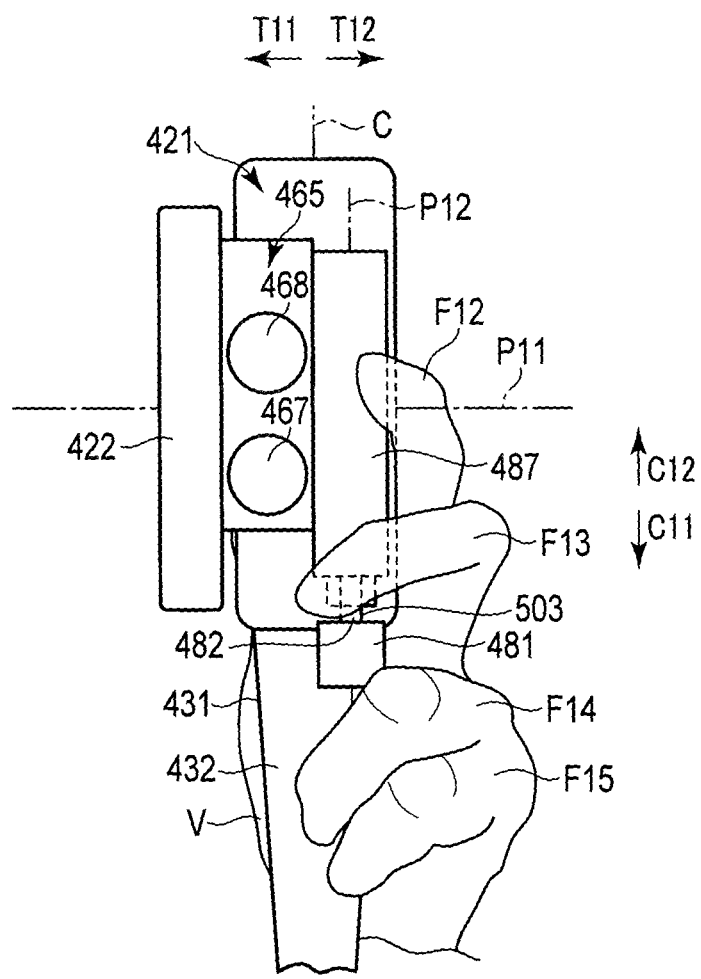
FIG. 32 is a schematic diagram seen from the first perpendicular direction side showing how a holding portion casing is held with the left hand.

Next, the functions and advantageous effects of the endoscope 402 which is the insertion instrument are described. When using the endoscope 402, the operator holds the holding portion casing 421 with the left hand. FIG. 31 and FIG. 32 show how the holding portion casing 421 is held with the left hand. FIG. 31 is a view from the first rotation axis direction side. FIG. 32 is a view from the first perpendicular direction side. As shown in FIG. 31 and FIG. 32, when the holding portion casing 421 is held, a palm V is located on the second rotation axis direction side of the holding portion casing 421. A thumb F11 is located closer to the second perpendicular direction side (the direction side of an arrow Q12 in FIG. 31) than the longitudinal axis C. A first finger F12, a second finger F13, a third finger F14, and a little finger F15 are located closer to the first perpendicular direction side (the direction side of an arrow Q11 in FIG. 31) than the longitudinal axis C. If the curving operation knob 422 which is the first operation input portion is rotated by use of, for example, the thumb F11 and the second finger F13, the first operation to curve the curving portion 407 in the first curving directions is input. If the curving operation dial 481 which is the second operation input portion is rotated by use of, for example, the second finger F13 and the third finger F14, the second operation to curve the curving portion 407 in the second curving directions is input. Further, the air/liquid operation button 467 and the suction operation button 468 are pressed by use of, for example, the first finger F12 and the second finger F13, and the switch operation to switch the actuation states of the functional units (the air/liquid supply valve 473 and the suction valve 475) is input.

Here, the curving operation dial 481 is located on the second rotation axis direction side than the button unit 465. Thus, the curving operation dial 481 which is the second operation input portion is located in the part on the second rotation axis direction side in the second casing outer surface 432. Even in the case of an operator with small hands, fingers such as the second finger F13 and the third finger F14 which perform the second operation with the curving operation dial 481 easily reach the curving operation dial 481. Thus, it is possible to ensure the operability of the second operation in the curving operation dial 481 which is the second operation input portion.

The housing portion 486 (the housing portion formation surface 487) is provided parallel to the second rotation axis direction side of the button unit 465. Thus, inside the holding portion casing 421, a space having a size sufficient to form the housing portion 486 is secured in the region located on the second rotation axis direction side in the vicinity of the button unit 465. As a result, a sufficient size of the housing portion 486 can be formed to house the shaft portion 482 and the rotation sensor 488.

When the first button 467 is pressed in the second perpendicular direction from the unpressed position to the switch position, the first press surface 471 of the first button 467 protrudes toward the first perpendicular direction side from the housing portion formation surface 487. Similarly, when the second button 468 is located at the switch position, the second press surface 472 of the second button 468 protrudes toward the first perpendicular direction side from the housing portion formation surface 487. Therefore, even if the housing portion formation surface 487 is provided parallel to the second rotation axis direction side of the button unit 465, fingers such as the first finger F12 and the second finger F13 which perform the switch operation with the first button 467 and the second button 468 do no have difficulty in reaching the first press surface 471 of the first button 467 and the second press surface 472 of the second button 468. Therefore, even if the housing portion formation surface 487 is provided parallel to the second rotation axis direction side of the button unit 465, the operability of the switch operation with the first button 467 and the second button 468 can be ensured.

The step portion 477 of the button unit 465 is located closer to the proximal direction side than the distal end of the outermost circumferential locus S0. Thus, when the second finger F13 is used to perform the first operation with the curving operation knob 422, it is difficult for the second finger F13 to interfere with the step portion 477. Thus, even if the button unit 465 is located in the part on the first rotation axis direction side in the second casing outer surface 432, the second finger F13 does not have difficulty in reaching the curving operation knob 422. Consequently, it is possible to ensure the operability of the first operation in the curving operation knob 422.

The curving operation dial 481 is located closer to the distal direction side than the distal end of the outermost circumferential locus S0. The shaft recess 503 which is recessed toward the second perpendicular direction is located between the step portion 477 and the distal end of the outermost circumferential locus S0 of the curving operation knob 422 in the longitudinal axis direction. In such a configuration, in the first operation in the curving operation knob 422 using the second finger F13, the second finger F13 passes through the region of the shaft recess 503 on the first perpendicular direction side, and it becomes difficult for the second finger F13 to interfere with the shaft portion 482. As a result, the second finger F13 easily reaches the curving operation knob 422, and the operability of the first operation in the curving operation knob 422 can be improved.

Fifth Embodiment: Modifications

Figure 33:
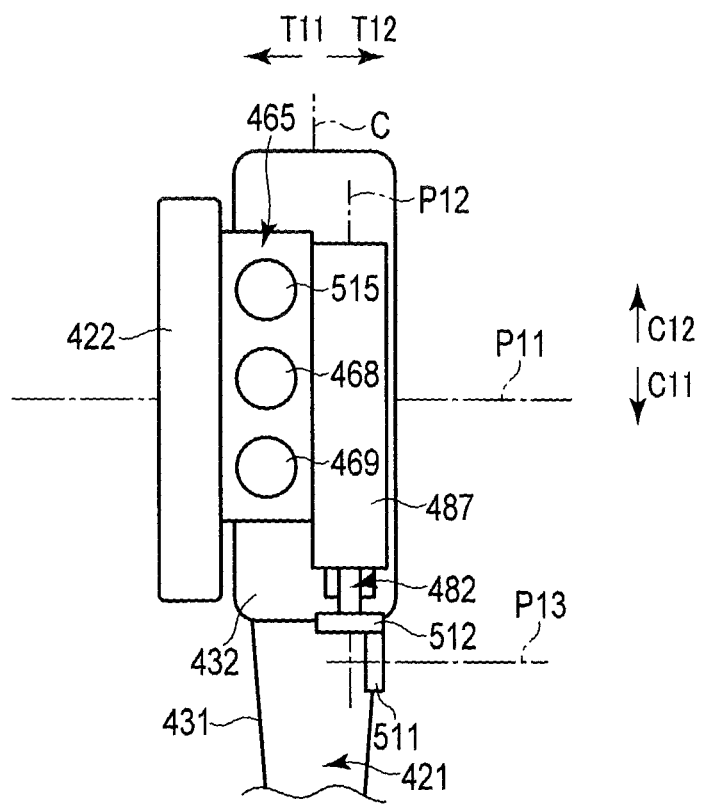
FIG. 33 is a schematic diagram in which a holding portion according to a first modification is seen from the first perpendicular direction side.

Although the curving operation dial 481 which is rotatable around the drive axis P12 is provided as the second operation input portion in the fifth embodiment, the second operation input portion is not limited to this. For example, in a first modification shown in FIG. 33, a curving operation rotor 511 which is rotatable around an operation axis P13 may be provided as the second operation input portion. The operation axis P13 is substantially perpendicular to the drive axis P12, and substantially parallel to the rotation axis P11. In the present modification, the shaft portion 482 is coupled to the curving operation rotor 511 via a spur gear 512. However, in the present modification as well as in the first embodiment, the shaft portion 482 extends toward the proximal direction side from the curving operation rotor 511 which is the second operation input portion along the drive axis P12 which crosses over the rotation axis P11.

The curving operation rotor 511 is located closer to the second rotation axis direction side than the button unit 465. The shaft rotation portion 485 of the shaft portion 482 rotates around the drive axis P12 by the input of the second operation in the curving operation rotor 511. In the present modification as well, the housing portion 486 and the housing portion formation surface 487 into which the shaft portion 482 is inserted are provided parallel to the second rotation axis direction side of the button unit 465.

In the present modification, an image adjustment button 515 is provided in the button unit 465 as an operation button in addition of the first button 467 and the second button 468. In the present modification, a switch portion (not shown) is provided in the vicinity of the button unit 465 inside the holding portion casing 421. One end of an electric signal line (not shown) is connected to the switch portion, and the other end of the electric signal line is connected to the image processing unit 411. If the image adjustment button 515 is pressed to the switch position toward the second perpendicular direction, the switch portion is turned on. Accordingly, the image processing state in the image processing unit 411 which is the functional unit provided separately from the curving portion (action portion) 407 is switched. That is, the switch operation to switch the actuation state of the image processing unit 411 which is the functional unit is input by the image adjustment button 515. For example, the white balance of an image to be generated by the image processing unit 411 changes as a result of the switch operation in the image adjustment button 515.

Figure 34:
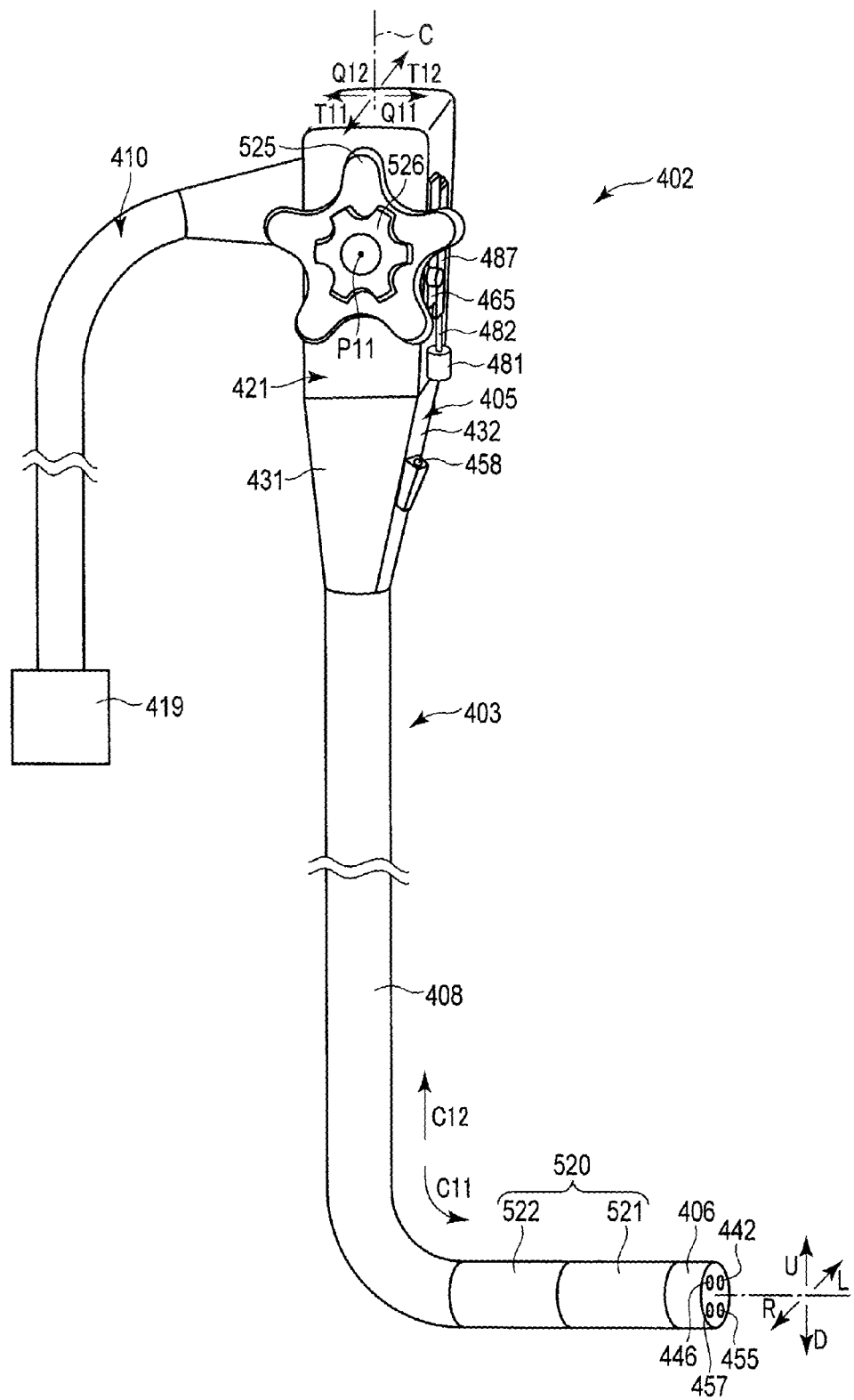
FIG. 34 is a perspective view schematically showing an endoscope according to a second modification.

In a second modification shown in FIG. 34 and FIG. 35, a two-step curving portion 520 may be provided as an action portion. The two-step curving portion 520 is located closer to the proximal direction side than the distal rigid portion 406, and located closer to the distal direction side than the flexible tube 408. The two-step curving portion 520 comprises a first curving portion 521, and a second curving portion 522 which is provided closer to the proximal direction side than the first curving portion 521. Therefore, in the longitudinal axis direction parallel to the longitudinal axis C, the second curving portion 522 is provided at a position different from that of the first curving portion 521.

The first curving portion 521 can curve in at least two directions perpendicular to the longitudinal axis C. In the present modification, the first curving portion 521 can curve in the two first curving directions (UD directions) and the two second curving directions (LR directions). The second curving portion 522 can curve in two directions perpendicular to the longitudinal axis C. In the present modification, the second curving portion can curve in the two first curving directions (UD directions). In the two-step curving portion 520 which is the action portion, the first curving portion 521 curves as the first action. Moreover, in the two-step curving portion 520, the second curving portion 522 curves as the second action.

In the present modification, a UD curving operation knob (first knob) 525 and an RL curving operation knob (second knob) 526 are provided as first operation input portions in the first casing outer surface 431 of the holding portion casing 421. An operation to curve the first curving portion 521 in the first curving directions (UD directions) is input by the rotation of the first knob 525 around the rotation axis P11. An operation to curve the first curving portion 521 in the second curving directions (RL directions) is input by the rotation of the second knob 526 around the rotation axis P11. That is, the first operation to operate the first action of the two-step curving portion 520 is input by the first knob 525 and the second knob 526 which are the first operation input portions. The configuration which transmits driving force for curving the first curving portion 521 in the first curving directions to the first curving portion 521 from the first knob 525, and the configuration which transmits driving force for curving the first curving portion 521 in the second curving directions to the first curving portion 521 from the second knob 526 are similar to the configuration which transmits driving force for curving the curving portion 407 in the first curving directions to the curving portion 407 from the curving operation knob 422 in the first embodiment. Therefore, these configurations are not described.

In the present modification, the button unit 465 is disposed in the second casing outer surface 432 to be provided parallel to the second rotation axis direction side of the first knob 525 which is the first operation input portion. As in the fifth embodiment, the curving operation dial 481 which is the second operation input portion is provided closer to the second rotation axis direction side than the button unit 465. In the present modification as well as in the fifth embodiment, the shaft portion 482 extends toward the proximal direction side from the curving operation dial 481 which is the second operation input portion along the drive axis P12 that crosses over the rotation axis P11. The housing portion 486 and the housing portion formation surface 487 into which the shaft portion 482 is inserted are provided parallel to the second rotation axis direction side of the button unit 465.

In the present modification, an operation to curve the second curving portion 522 in the first curving directions (UD directions) is input by the rotation of the curving operation dial 481. That is, the second operation to operate the second action of the two-step curving portion 520 is input by the curving operation dial 481 which is the second operation input portion. The shaft rotation portion 485 of the shaft portion 482 rotates around the drive axis P12 by the input of the second operation. The configuration which uses an electric motor (not shown) to generate driving force for curving the second curving portion 522 in the first curving directions on the basis of the input of the second operation is similar to the configuration which uses the electric motor 492 to generate driving force for curving the curving portion 407 in the second curving directions on the basis of the input of the second operation in the fifth embodiment. The configuration which transmits the driving force to the second curving portion 522 from the electric motor (not shown) is similar to the configuration which transmits the driving force to the curving portion 407 from the electric motor 492 in the fifth embodiment. Therefore, these configurations are not described.

In the second modification, the first curving portion 521 may be able to curve in the first curving directions (UD directions) alone without curving in the second curving directions. In this case, the second knob 526 is not provided, and the first knob 525 alone is provided.

Although the endoscope 402 has been described as the insertion instrument in the fifth embodiment and the modifications, the insertion instrument is not limited to the endoscope 402. For example, the configuration described above may be applied to a manipulator which is an insertion instrument.

In the embodiments and the modifications described above, the action portions 407, 520 which perform the first action and the second action are provided in the insertion portion 403. The holding portion 405 is provided with the first operation input portion 422, 525, 526 to which the first operation to operate the first action of the action portions 407, 520 is input by the rotation around the rotation axis P11 perpendicular to the longitudinal axis C. The holding portion casing 421 comprises the first casing outer surface 431 which faces in the first rotation axis direction T11 and in which the first operation input portion 422, 525, 526 is disposed, and the second casing outer surface 432 facing in the first perpendicular direction Q11. In the second casing outer surface 432, the button unit 465 is disposed to be provided parallel to the second rotation axis direction T12 side of the first operation input portion 422, 525, 526. In the second casing outer surface 432, the second operation input portion 481, 511 to which the second operation to operate the second action of the action portions 407, 520 is input is provided closer to the second rotation axis direction T12 side than the button unit 465. The shaft portion 482 extends toward the proximal direction C12 side from the second operation input portion 481, 511 along the drive axis P12 which crosses over the rotation axis P11. The housing portion formation surface 487 of the second casing outer surface 432 forms the housing portion 486 into which the shaft portion 482 is inserted inside the holding portion casing 421 so that the housing portion formation surface 487 is provided parallel to the second rotation axis direction T12 side of the button unit 465.

While the embodiments and modifications of the present invention have been described above, the present invention is not limited to the embodiments and modifications described above, and needless to say, various modifications can be made without departing from the spirit of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:

1. An insertion instrument comprising:
  an insertion portion which extends from a proximal direction to a distal direction along a longitudinal axis, the insertion portion comprising an action portion which performs a first action and a second action different from the first action; and
  a holding portion provided on a proximal direction side of the insertion portion, the holding portion comprising a holding portion casing, and a first operation input portion which operates the first action of the action portion by rotating relative to the holding portion casing around a rotation axis extending in a direction different from the longitudinal axis,
  wherein the holding portion casing comprises
    a first casing outer surface which faces a first rotation axis direction and in which the first operation input portion is disposed, when one of directions parallel to the rotation axis is the first rotation axis direction, and a direction opposite to the first rotation axis direction is a second rotation axis direction, and
    a second casing outer surface which faces in a first perpendicular direction, when one of directions perpendicular to the longitudinal axis and perpendicular to the rotation axis is the first perpendicular direction, and a direction opposite to the first perpendicular direction is a second perpendicular direction, and
  the holding portion comprises
    a button unit comprising an operation button to which a switch operation to switch the actuation state of a functional unit provided separately from the action portion is input, the button unit being disposed in the second casing outer surface to be provided parallel to the second rotation axis direction side of the first operation input portion,
    a second operation input portion which is disposed closer to the second rotation axis direction side than the button unit in the second casing outer surface and to which a second operation to operate the second action of the action portion is input by rotating,
    a shaft portion extending toward the proximal direction side from the second operation input portion along a drive axis which crosses over the rotation axis, the shaft portion comprising a shaft rotation portion which rotates around the drive axis by the input of the second operation in the second operation input portion, and
    a housing portion formation surface which is provided closer to the second rotation axis direction side than the button unit in the second casing outer surface and which forms a housing portion for the insertion of the shaft portion inside the holding portion casing to be protruding in the first perpendicular direction so that a center of the drive axis of the shaft portion is disposed closer to the second rotation axis direction side than the button unit.

2. The insertion instrument according to claim 1, wherein the operation button comprises a press surface which is pressed to the second perpendicular direction by the input of the switch operation and which protrudes toward the first perpendicular direction side from the housing portion formation surface when the operation button is pressed to the switch position which is a position where the actuation state of the functional unit is switched.

3. The insertion instrument according to claim 1, wherein the button unit comprises a step portion which forms the distal end of the button unit and which forms steps in the second casing outer surface in the first perpendicular direction and the second perpendicular direction, the step portion being located closer to the proximal direction side of the insertion portion than the distal end of an outermost circumferential locus when a rotation locus on the outer circumferential end of the first operation input portion is the outermost circumferential locus.

4. The insertion instrument according to claim 3, wherein the second operation input portion is located further distally than the distal end of the outermost circumferential locus of the first operation input portion.

5. The insertion instrument according to claim 3, wherein the shaft portion comprises a shaft exposing portion which protrudes distally from the housing portion and which is exposed to the outside of the holding portion casing in the second casing outer surface, and the shaft exposing portion comprises a shaft recess which is located between the step portion and the distal end of the outermost circumferential locus of the first operation input portion in the longitudinal axis direction parallel to the longitudinal axis and which is recessed toward the second perpendicular direction.

6. The insertion instrument according to claim 1, wherein the holding portion comprises a rotation sensor which is provided in the housing portion and which detects the rotation state of the shaft rotation portion.

7. An insertion apparatus comprising:
the insertion instrument according to claim 6;
a driving source which generates driving force for the second action of the action portion by the supply of electric power; and
an electric power controller which controls the state of the supply of the electric power to the driving source on the basis of the rotation state of the shaft rotation portion detected by the rotation sensor.

8. The insertion instrument according to claim 1, wherein the action portion comprises a curving portion configured to curve in first curving directions which are two directions perpendicular to the longitudinal axis and in second curving directions which are two directions perpendicular to the longitudinal axis and perpendicular to the first curving directions, the curving portion curving in the first curving directions as the first action and curving in the second curving directions as the second action.

9. The insertion instrument according to claim 1, wherein the holding portion comprises a path extending through the holding portion casing, and a valve which is the functional unit disposed in the path, and the operation button comprises a valve operation button which switches the open/close state in the path by the valve.

10. An insertion apparatus comprising:
the insertion instrument according to claim 1;
an image pickup device which is provided in the insertion portion and which images a subject; and
an image processing unit which is the functional unit to perform image processing on the basis of subject figure imaged by the image pickup device,
wherein the operation button comprises an image adjustment button which switches an image processing state in the image processing unit.

* * * * *